(12) United States Patent
Bradshaw et al.

(10) Patent No.: US 6,197,260 B1
(45) Date of Patent: Mar. 6, 2001

(54) REAGENT PACKAGE

(75) Inventors: Randolph Bradshaw, Brewster, NY (US); Andrew Oakes, Harrington Park, NJ (US); Nicholae Dumitrescu, Stamford, CT (US); Robert L. Berger, Bound Brook, NJ (US); William M. Jameson, Cranbury, NJ (US); Chris Robinson, Lawrenceville, NJ (US); James R. Laskey, Chestertown, MD (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/115,283

(22) Filed: Jul. 14, 1998

Related U.S. Application Data

(63) Continuation-in-part of application No. 08/985,759, filed on Dec. 5, 1997, now Pat. No. 6,043,097.

(51) Int. Cl.[7] .............................. B01L 11/00; B65D 3/26
(52) U.S. Cl. .................... 422/101; 210/295; 210/321.78; 210/331
(58) Field of Search ..................... 422/99, 101; 210/295, 210/314, 315, 321.78, 324, 331

(56) References Cited

U.S. PATENT DOCUMENTS

| | | |
|---|---|---|
| 4,455,280 | 6/1984 | Shinohara et al. . |
| 4,707,450 | 11/1987 | Nason . |
| 4,876,068 | 10/1989 | Castaneda . |
| 4,900,440 * | 2/1990 | Zeigler et al. ...................... 422/101 |
| 5,271,897 | 12/1993 | Wurschum et al. . |
| 5,289,930 | 3/1994 | Inouye . |

* cited by examiner

Primary Examiner—Lyle A. Alexander
(74) Attorney, Agent, or Firm—Andrew L. Klawitter, Esq.; Rodman & Rodman

(57) ABSTRACT

The reagent package includes a container housing section and a container lid that are sealed together to define one or more inside chambers. An opening in the container lid provides access to a corresponding chamber. The chamber opening is controlled by a valve that is pivotable from an open position to a closed position and vice versa. When the valve is in an open position the container chamber can be accessed through the valve with an aspiration probe and a dispensation probe. The reagent package accommodates a filter screen member and a glass ampoule in the container chamber. The glass ampoule contains one reagent ingredient, which can be a dry powder and the space within the chamber outside the glass ampoule can contain a reconstituting liquid. When the reagent package is ready for use a pressure force is imposed on the outside wall of the chamber adjacent the glass ampoule to crush the ampoule and permit the liquid within the chamber to mix with the dry powder released from the glass ampoule. Drainage channels can be provided in the floor of the container to direct the flow of liquid at the container floor into a filter well. Micro-slits are provided in the wall of the filter well and complementary engaging wall of the filter. Liquid can thus flow into the filter well through the micro-slits.

10 Claims, 23 Drawing Sheets

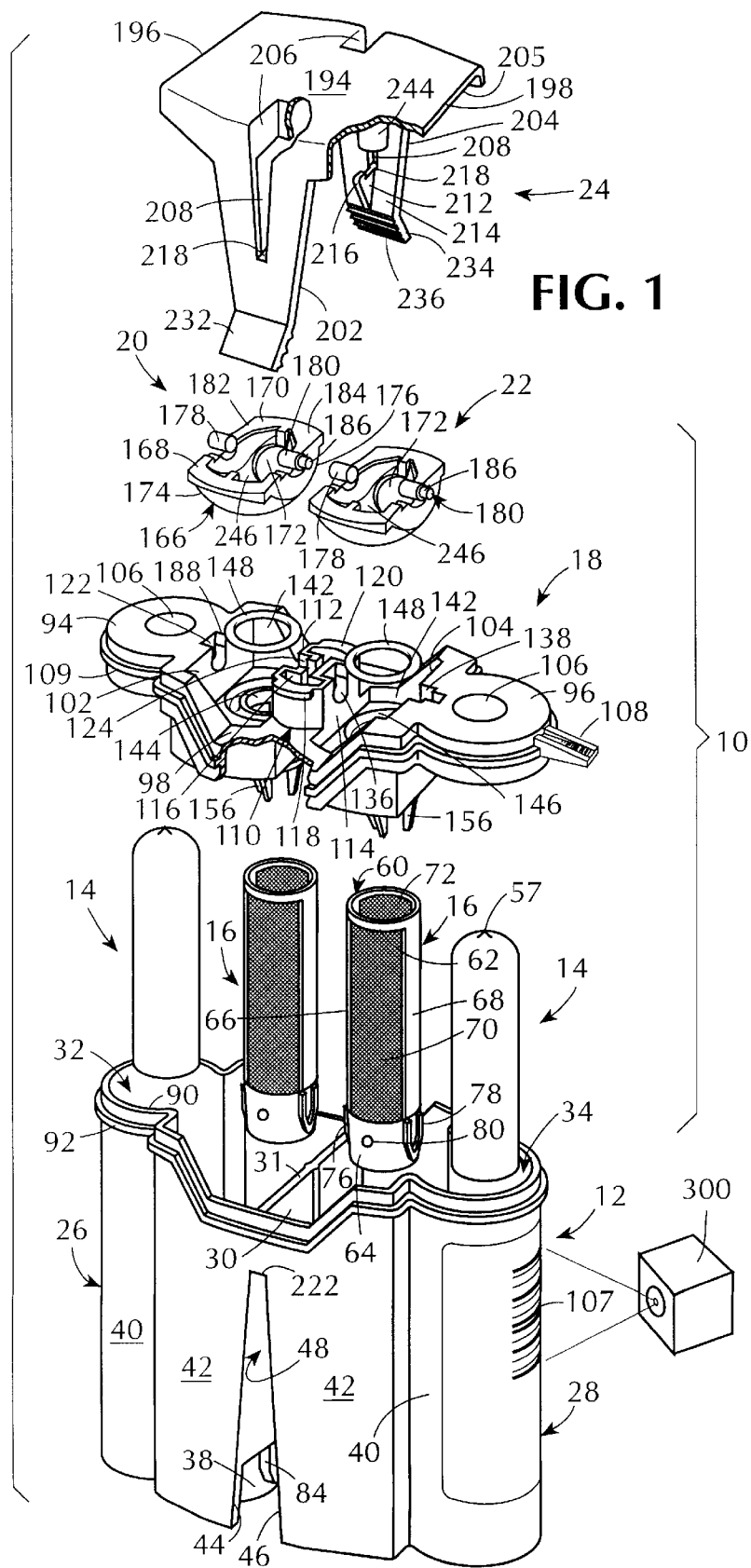

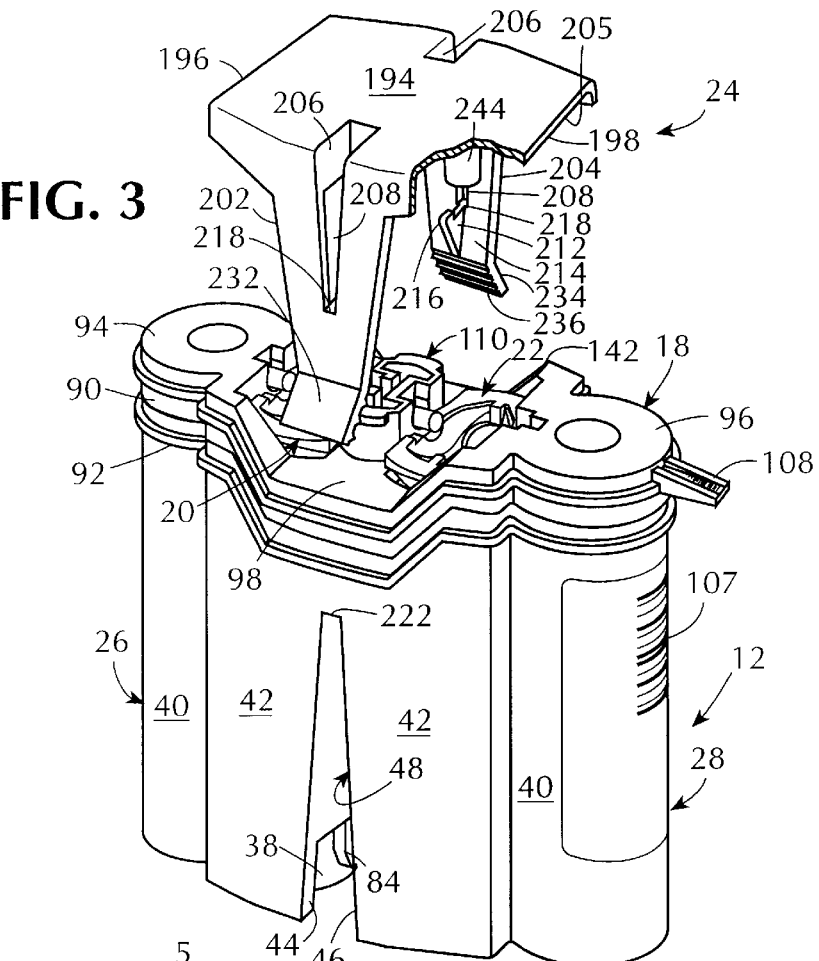

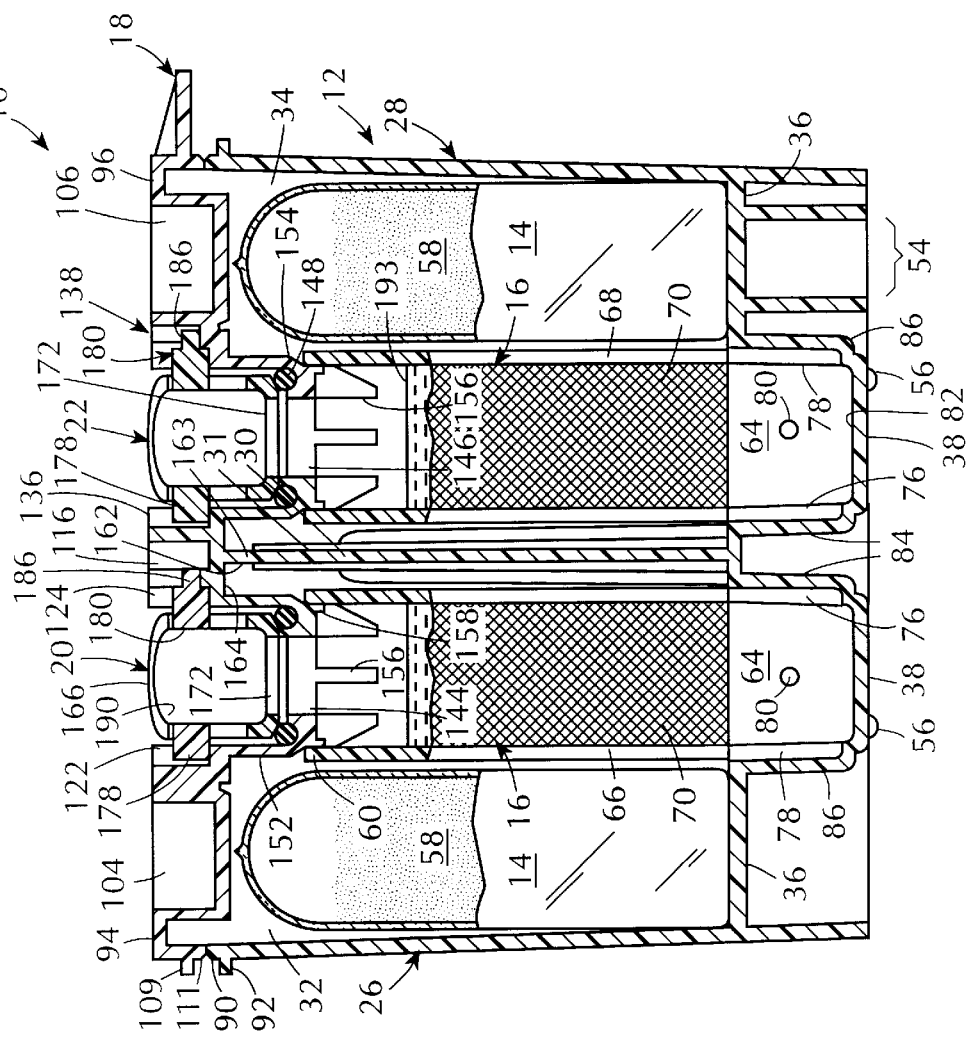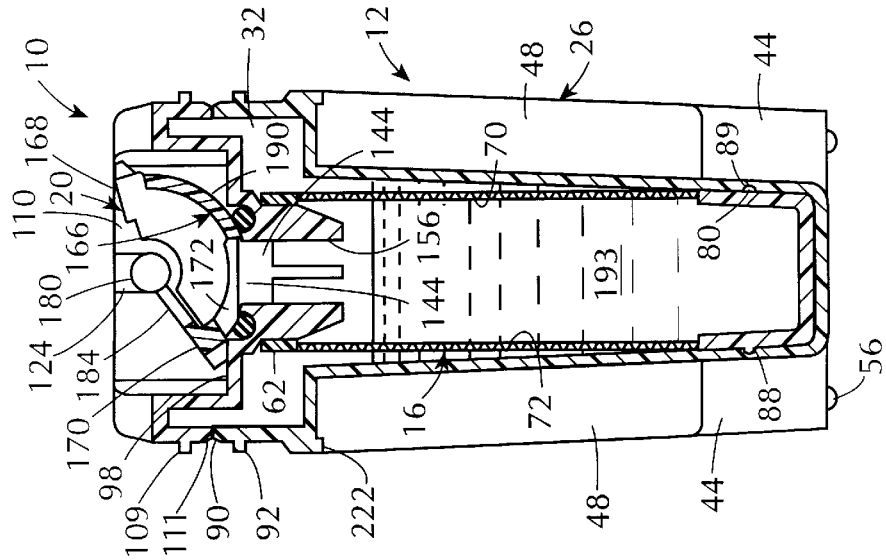

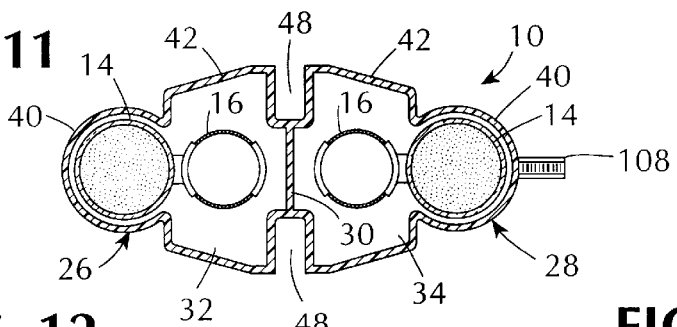
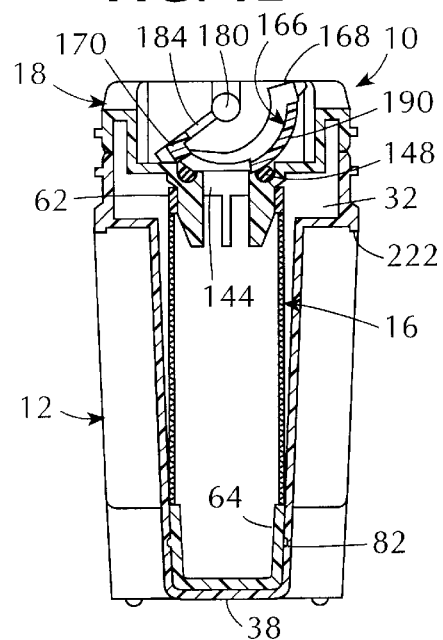
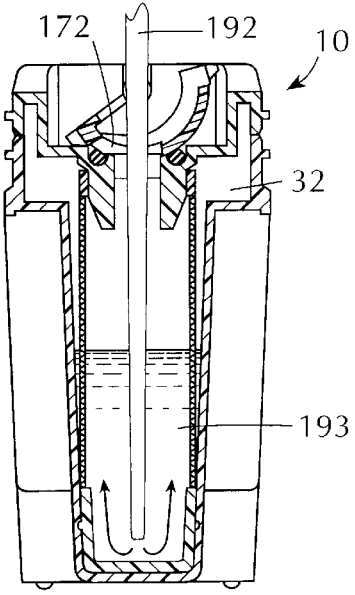
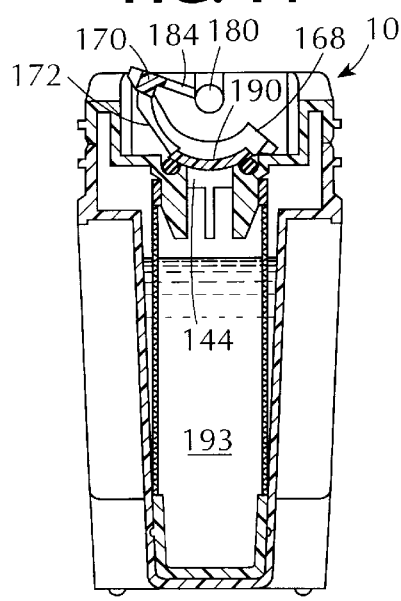
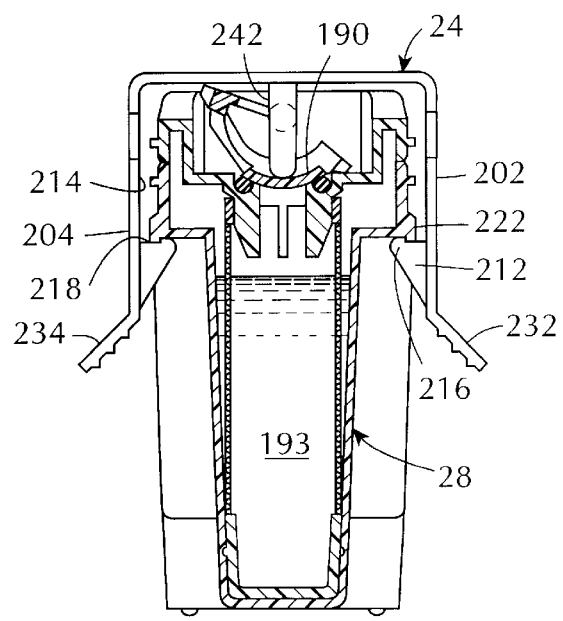

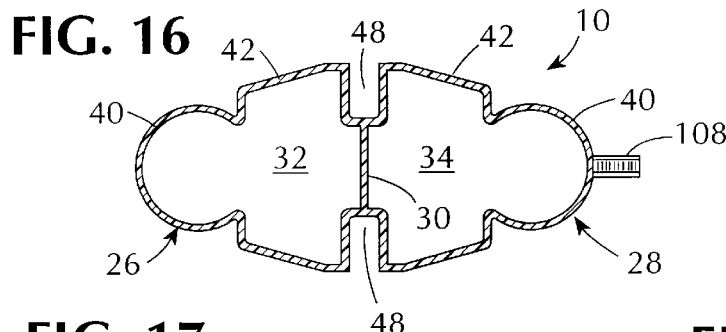
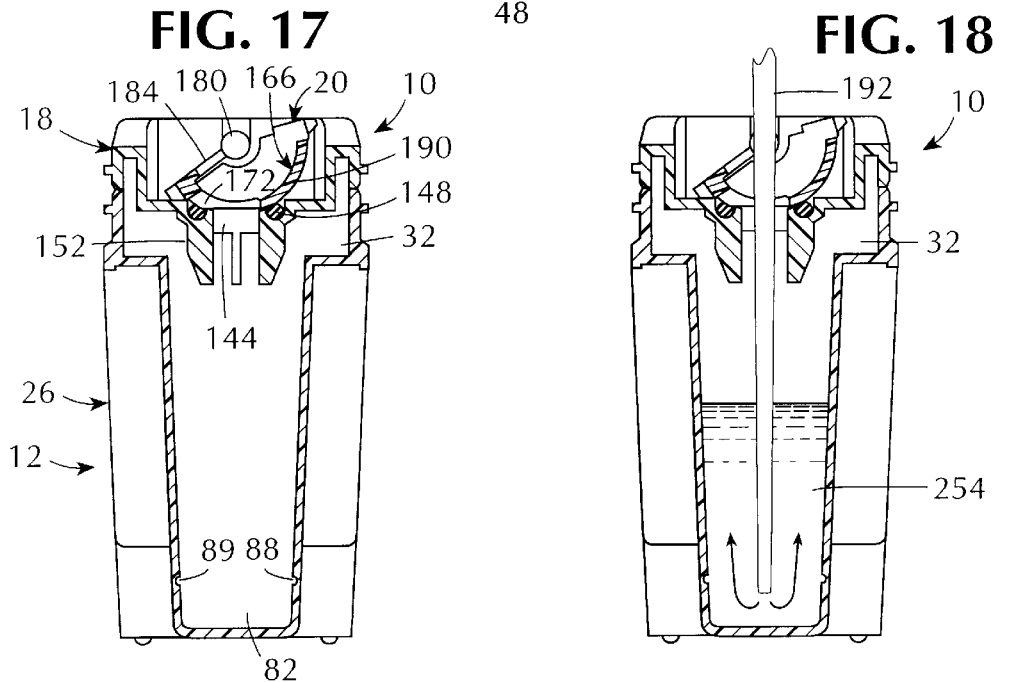
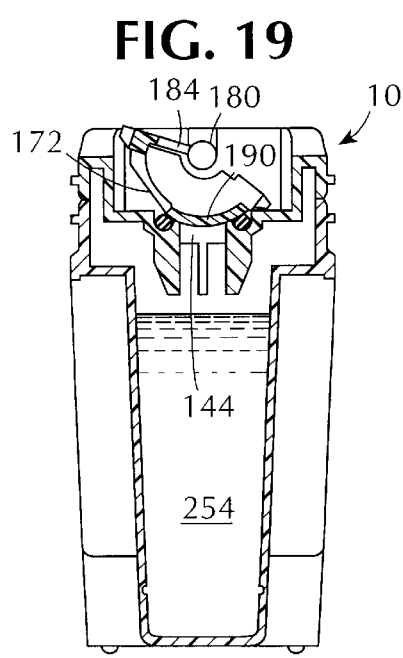
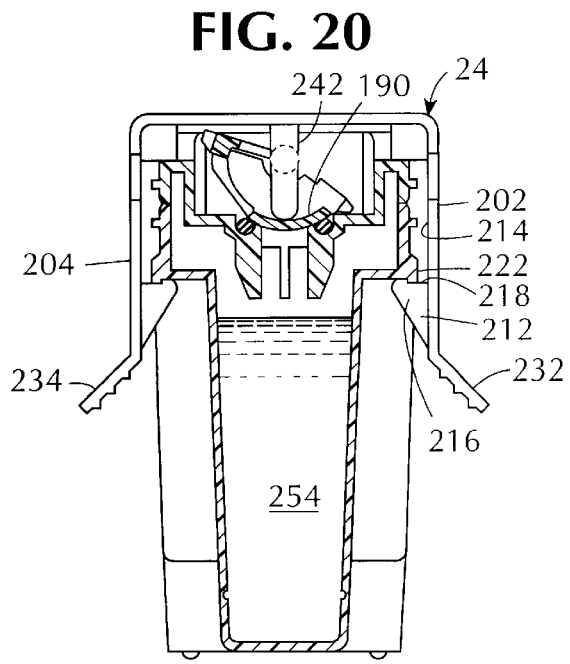

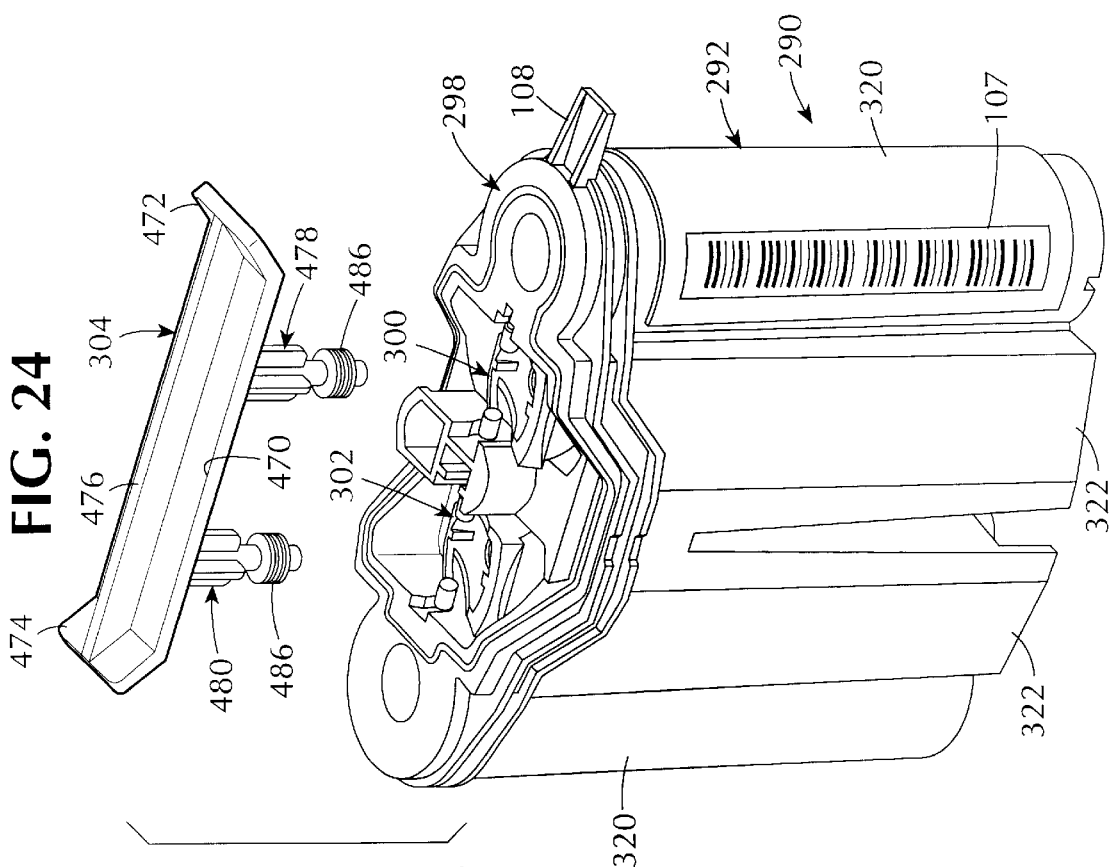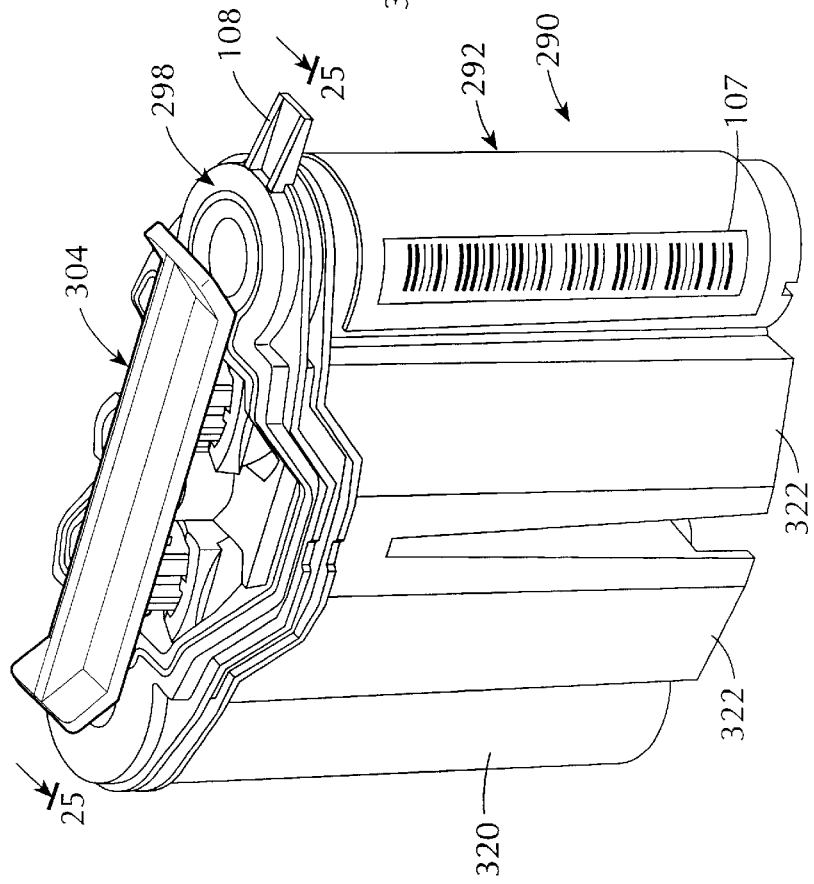

REAGENT PACKAGE

This application is a continuation-in-part of application Ser. No. 08/985,759 filed Dec. 5, 1997 now U.S. Pat. No. 6,043,097.

BACKGROUND OF THE INVENTION

This invention is directed to reagent packaging devices for storing one or more ingredients or reagents separate from one another in a single reagent package for subsequent mixing in the reagent package, and more particularly to a novel reagent package having a valve controlled opening that can be sealed independently of the valve. The invention is also directed to a reagent package having a novel liquid flow director system for directing substantially all liquid on a floor of the package into a liquid aspiration area and for preventing any minute glass particles that may surround the liquid aspiration area from entering the aspiration area.

Automated sample analysis systems as disclosed in U.S. Pat. Nos. 5,268,167 and 5,399,497 can perform a variety of different tests on a test subject, such as a serum sample, in a relatively short period of time. Generally the serum sample is separated into a predetermined number of segregated portions and a different test is usually performed on each segregated portion of the serum sample. It is thus common practice to divide the serum sample into a series of separate isolated sample segments that correspond to each separate test. The isolated sample segments are enabled to co-act with specific reagents to produce an analyzable reaction that forms the basis for a test result.

Different reagents will produce different test results on respective sample segments and the compendium of the separate test results provide a body of information or data relating to the characteristics of the serum sample.

As used herein, the term reagent is intended to refer to a single reagent, a mixture of two or more reagents and/or a mixture of reagent with a reconstituting liquid.

Reagents for sample analysis systems are preferably used in liquid form to permit allotment of a precise predetermined amount of reagent to each sample segment and to help ensure that the reaction between the reagent and the serum sample is uniform. Generally, the reagent is diluted to a desired concentration before it is permitted to co-act with a serum sample.

It is well known that some reagents used in sample analysis systems have a limited shelf life especially if produced as a solution of one or more reagent components. Therefore, optimum test results between a reagent and a serum sample are usually obtained if the reagent is dissolved or diluted shortly before being used for test purposes.

Since the shelf life of a reagent in dry form is usually longer than the shelf life of the reagent in a liquid condition it is common practice to maintain a reagent in dry condition in a reagent mixing package. In some instances, the mixing package is arranged to hold in segregated condition a dry reagent component and a liquid reconstituting component. When use of the reagent is desired, the components are intermixed within the package.

One known reagent package such as shown in U.S. Pat. No. 4,515,753 includes a reagent in lyophilized powder form in a first breakable capsule and a reconstituting liquid for the reagent in a second breakable capsule. The capsules are broken by compressing the package to release the contents of each capsule for mixing within the package. An outlet port in the package permits outside access to the mixed ingredients. Although this reagent package provides a freshly mixed reagent for immediate use in a sample analysis system, it is difficult to seal the package once the ingredients have been mixed. This package also does not permit long term preservation of liquid that is openly contained in the package and therefore the reconstituting liquid must be maintained in a capsule.

It is thus desirable to provide a reagent package that can be sealed when it is in storage awaiting use and also provide for sealing of the package after the package contents are mixed for use.

Generally, the liquid mixture contained in the reagent package is one of the most expensive consumable constituents of a sample analysis system. For example the contents of an individual reagent package can cost approximately $600 to $1,000 for approximately 20 to 25 milliliters of mixed reagent.

It is thus beneficial to be able to conveniently withdraw substantially all of the liquid reagent that is mixed in a reagent package. It is also desirable that such withdrawal of reagent be free of any fragmentary glass particles that result from breakage of a glass ampoule in the package after the arnpoule is broken to release a constituent of the reagent mixture.

It is also desirable to provide a reagent package for one or more reagent components wherein the package has a valve controlled opening that can also be sealed independently of the valve, and which package permits use of substantially all of the mixed ingredients in the reagent package without contamination from glass particles after an ampoule is broken in the reagent package.

OBJECTS AND SUMMARY OF THE INVENTION

Among the several objects of the invention may be noted the provision of a novel reagent package having a valve controlled opening, a novel reagent package having a valve controlled opening wherein the valve can be locked in a closed position with a locking clip to provide a substantially leak-tight seal, a novel reagent package having a valve controlled opening wherein the valve in a movable condition, without the locking clip provides an evaporation barrier for liquid contained in the package when the valve is in a closed position, a novel reagent package having a valve controlled opening wherein the valve can be rendered movable with respect to the container opening to optionally select open and closed positions of the reagent package, a novel reagent package that can accommodate a breakable ampoule with one reagent and an openly stored reconstituting liquid, a novel reagent package having a valve controlled opening wherein the valve can be locked in a closed position to provide a substantially leak tight seal that permits long term storage of a liquid reagent, a novel reagent package with a breakable ampoule and a filter screen that is structured to resist damage from broken glass, a novel reagent package which can be deformed to break a frangible ampoule inside the package without damaging the package and without damaging a valve provided on the package, a novel reagent package having two separate non-communicable chambers to constitute a dual reagent package, a novel reagent package that provides valve controlled access to substantially all liquid reagent in the package, a novel reagent package that accommodates a breakable ampoule and permits aspiration of reagent from the broken ampoule without the glass particles, and a novel method of providing controlled access to a reagent in a package.

Further objects include the provision of a novel reagent package having a valve controlled opening that can be sealed independently of the valve to provide a tighter seal than the valve provides, a novel reagent package with flow channels formed in the floor of the package that are directed to a liquid aspiration area, and a novel means for preventing any minute fragmentary particles that may surround the liquid aspiration are from entering the liquid aspiration area. Other objects and features of the invention will be in part apparent and in part pointed out hereinafter.

In accordance with the present invention, the reagent package includes a container having an inside chamber and a restrictable opening to the chamber. A valve is positioned on the container to control the opening. The valve has a valve closed position to close off and seal the opening and a valve open position to permit access to the container chamber through the container opening. Preferably the valve is a rocker valve which is pivotable about a pivot axis that is spaced above the container opening.

In a preferred embodiment of the invention the reagent package is a dual package and includes two separate chambers that are non communicable with each other. Each chamber has a separate opening controlled by a separate rocker valve. The rocker valves are identical and have pivots that are cantilevered at the end of pivot support arms to permit deflection between the valve face and the valve pivots.

When the reagent package is in a valve closed position reagent materials inside the container cannot be accessed. Also when the reagent package is in a valve closed position a locking clip can be placed on the package to further secure the valves against the container opening thereby enhancing the valve seal. The locking clip enables ingredients of the reagent package to be stored without degradation for approximately two years under refrigeration.

In one embodiment of the invention the reagent package includes a hollow filter screen member in each chamber and a breakable glass ampoule in each chamber. The glass ampoule contains one reagent ingredient and is preferably in a dry lyophilized condition. The internal chamber space outside the glass ampoule can accommodate a reconstituting liquid. When it is desired to use the ingredients of the reagent package, a compression force is applied to the outside wall of the reagent package proximate the glass ampoule to crush the ampoule. The contents of the ampoule are thus released and can mix inside the package chamber with the reconstituting liquid. If desired, the ampoule can contain a liquid ingredient.

The reagent package also includes a well portion that defines the lowest point in the package. The well portion receives a bottom portion of the filter screen member and also receives through the screen of the filter member the mixed ingredients of the reagent package. The screen member filters out any broken glass from the crushed ampoule. The mixed ingredients of the reagent package are aspirated through the hollow space of the filter member. As the chamber ingredients are depleted during aspiration of reagent the unused reagent tends to flow into the bottom of the screen member in the filter well where it can be easily aspirated thus minimizing or eliminating any waste of reagent material.

The invention also includes a method of providing controlled access to a reagent. A closed container is provided with a valve controlled opening to maintain the container in a sealed condition when the valve is in a closed position and to provide access to the container when the valve is in an open position. The method further includes arranging the valve as a rocker valve at the opening of the container such that the valve is pivotable about an axis that is spaced from the container opening. The rocker valve can thus be pivoted from the valve open position to the valve closed position and vice versa. The rocker valve is provided with a valve face having opposite ends. Pivot means for the rocker valve connect to only one end of the valve face in cantilever arrangement. The cantilever arrangement permits the valve face to be deflectable from the pivot axis and permits pressure sealing of the valve face against the opening in the container.

In another embodiment of the invention the floor portion of the reagent package is formed with channels directed toward the filter well. The channels have a lowermost end portion at the periphery of the filter well. Downwardly directed micro-slits are formed in the bottom portion of the filter and also in the peripheral wall of the filter well. The micro-slits in the filter well alien with the channels formed in the floor of the reagent package. The micro-slits formed in the bottom portion of the filter member have an upper end that is communicable with the fluid chamber surrounding the filter member and a lower end that communicates with the space in the filter well below the filter member.

The bottom portion of the filter member and the peripheral wall of the filter well are of complimentary shape. The bottom portion of the filter also includes a deflectable circumferential toe flange that contacts the peripheral wall of the filter well when the filter is installed in the filter well.

The bottom portion of the filter member can thus make surface contact with the peripheral wall of the filter well due to the complimentary shape of the bottom portion of the filter member and the peripheral wall of the well. The bottom portion of the filter member can also make circumferential line contact with the peripheral wall of the filter well where the circumferential toe portion of the filter contacts the wall of the filter well.

Under this arrangement liquid that is on the floor of the reagent package can drain into the filter well through the floor channels and through the micro-slits at the bottom portion of the filter member and in the wall of the filter well. Fluid on the floor of the reagent package may also seep between the surface contact area of the filter and the filter well and between the circumferential line contact area between the bottom portion of the filter member and the wall of the filter well.

However, any fragmentary solid glass material in the mixing chamber of the reagent package due to breakage of the glass ampoule is prevented from entering the filter well because of the surface contact between the filter and the filter well and because of the circumferential line contact between the filter member and the filter well wall.

The valve of the reagent package which is pivotable on the package, has a cover-like closure or sealing portion and an open portion. The valve is movable to a closed position wherein the sealing portion closes the container opening. The valve is also movable to an open position wherein the open portion of the valve aligns with the container opening to expose the container opening.

In still another embodiment of the invention a plug member has a plug portion engagable in the container opening when the valve is in the open position. The plug member plugs the container opening when the reagent package is being stored or shipped and is not yet ready for use. The engagement of the plug member in the container opening through the open portion of the valve prevents the valve from moving.

When the reagent package is ready for use the plug member is removed from the container opening thereby permitting movement of the valve. The valve can then be moved to the closed position wherein the sealing portion of the valve covers the container opening. The reagent package can then be prepared for internal ampoule breakage and reagent mixing while the broken ampoule remains in place in the reagent package.

The invention accordingly comprises the constructions and method hereinafter described, the scope of the invention being indicated in the claims.

DESCRIPTION OF THE DRAWINGS

In the accompanying drawings,

FIG. 1 is an exploded perspective view of a reagent package and a locking clip incorporating one embodiment of the invention;

FIGS. 3 and 4 are perspective views prior to and after assembly of the locking clip to the reagent package;

FIGS. 7 and 8 are sectional views similar to FIGS. 5 and 6 with the locking clip removed and the rocker valve in an open position;

FIG. 11 is a simplified schematic top plan sectional view of the reagent package;

FIGS. 12–15 are sectional views corresponding to FIG. 7 showing the reagent package with the rocker valve in an open position (FIG. 12), infusion of liquid into the reagent package through the open rocker valve (FIG. 13), closing of the reagent package by movement of the rocker valve to a valve closed position (FIG. 14) and locking of the rocker valve in the valve closed position with the locking clip (FIG. 15);

FIG. 16 is a simplified schematic top plan sectional view thereof without the filter screen and glass ampoule;

FIGS. 17–20 are sectional views in elevation of the reagent package, without the filter screen and glass ampoule, showing the rocker valve in an open position (FIG. 17), infusion of liquid into the reagent package through the open rocker valve (FIG. 18), closing of the reagent package by movement of the rocker valve to a valve closed position (FIG. 19) and locking of the rocker valve in the valve closed position with the locking clip (FIG. 20);

FIG. 23 is a perspective view of another embodiment of the invention, in assembled condition with a plug member installed therein;

FIG. 24 is a view similar to FIG. 23 with the plug member removed from the reagent package;

Corresponding reference numbers indicate corresponding parts throughout the several views of the drawings.

DETAILED DESCRIPTION OF THE INVENTION

Figure 2A:
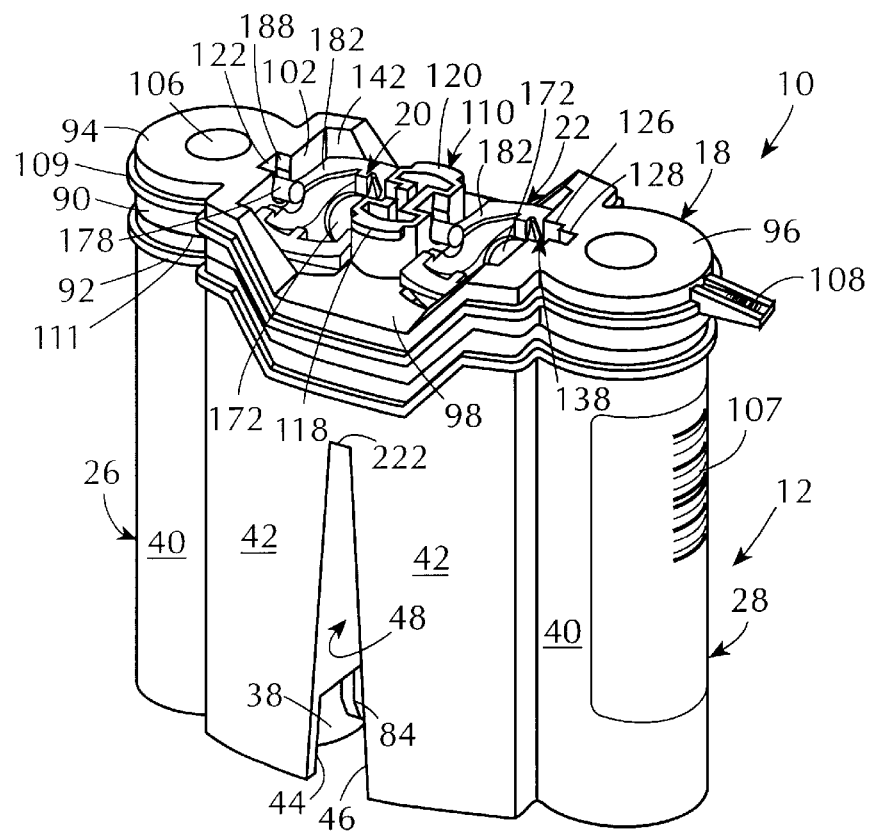
FIG. 2A is a perspective view thereof in assembled condition without the locking clip.

A reagent package incorporating one embodiment of the invention is generally indicated by the reference number 10 in FIGS. 1 and 2A.

The reagent package 10 includes a container housing section 12 that accommodates two glass ampoules 14, 14, two filter screens 16, 16, and a container lid 18 that supports two identical rocker valves 20 and 22. A locking clip member 24 maintains the rocker valves 20 and 22 of the reagent package 10 in a locked and leak-proof condition during shipping and storage.

It should be noted that the reagent package 10 is a dual package with two packaging sections 26 and 28 (FIGS. 2A and 5) arranged side-by-side. Although the packaging sections 26 and 28 are formed as an integral unit of the reagent package 10 the contents of either packaging section 26 and 28 cannot communicate with the contents of the other packaging section. Each packaging section 26 and 28 is similar in structure and function. If desired any of the packaging sections 26 and 28 can be formed as a separate reagent package.

The container housing section 12 includes a partition wall 30 that divides the container interior into two separate container chambers 32 and 34. Each of the container chambers 32 and 34 can acconunodate a frangible ampoule 14 and a filter screen 16.

Figure 5:
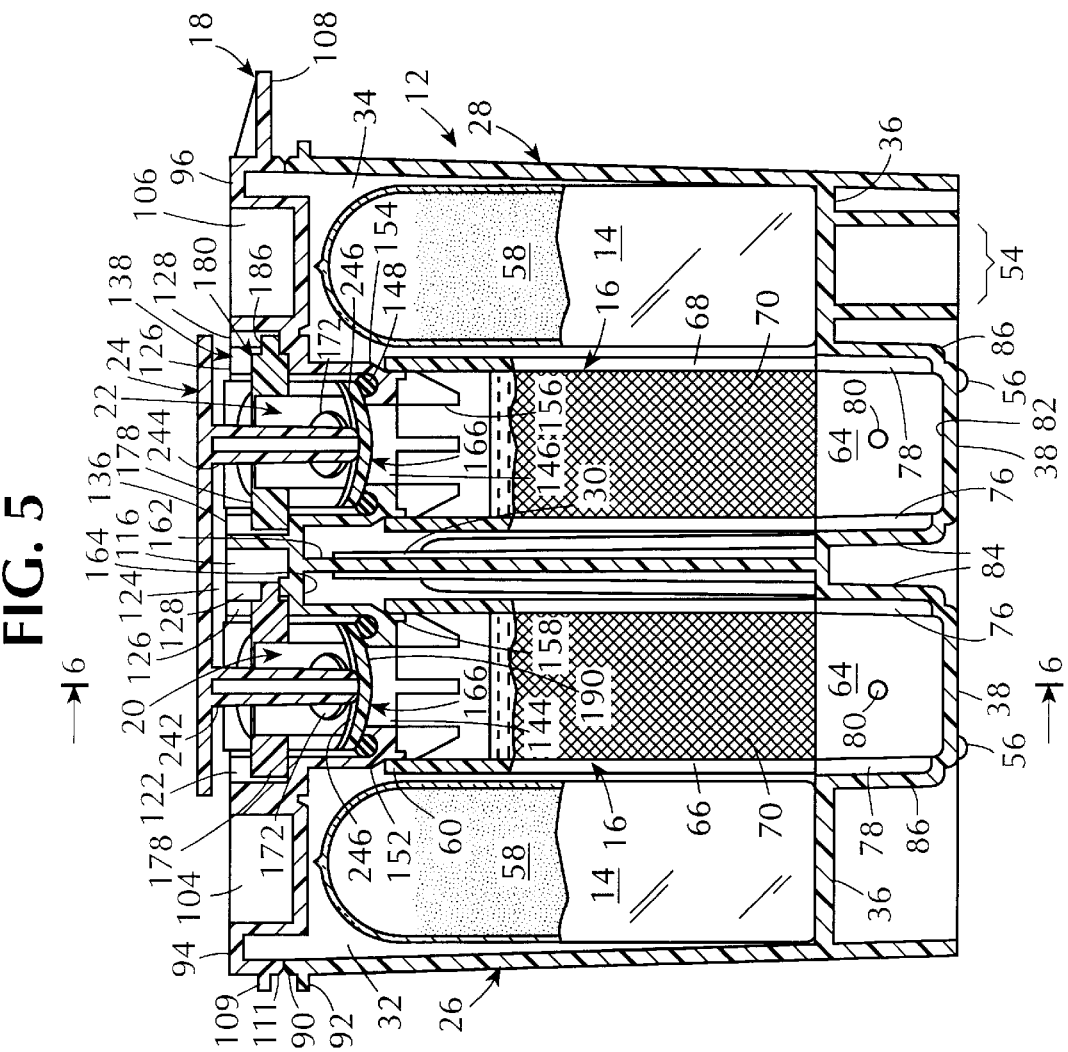
FIG. 5 is a sectional view taken on the line 5—5 of FIG. 4, with a rocker valve thereof in a closed position.

Referring to FIGS. 5 and 8 each container chamber 32 and 34 has an upper stepped base portion 36 that supports the ampoule 14 and a lower stepped base portion 38 that supports the filter screen member 16. A portion 40 (FIGS. 1 and 11) of the container housing section 12 which partially and closely surrounds each ampoule 14 is of generally cylindrical shape whereas a portion 42 of the container housing section 12 that partially confines each filter screen member 16 is of generally trapezoidal shape. The vertical walls of the housing section 12 are slightly inclined as most clearly shown in FIG. 7.

Figure 2B:
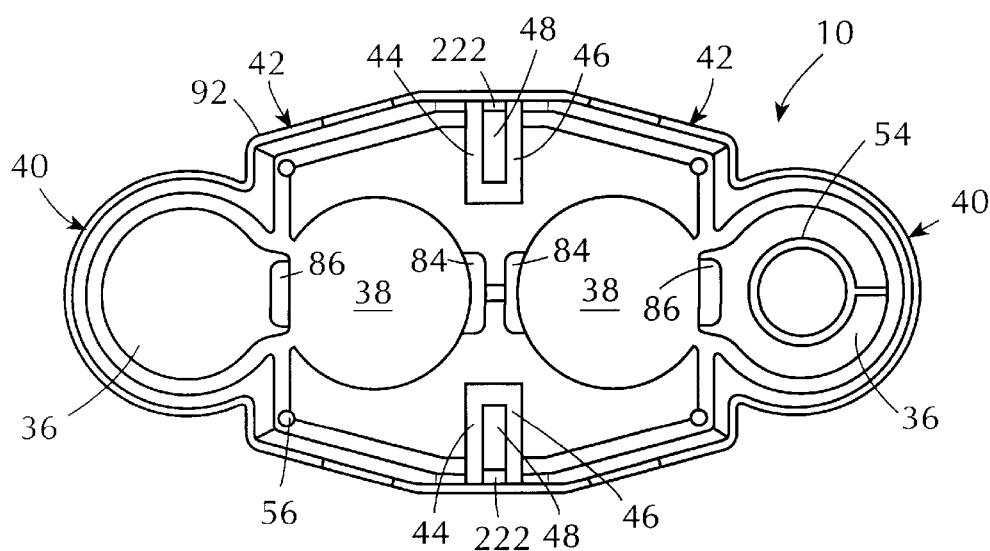
FIG. 2B is a bottom plan view therof.

Opposite sides of the container housing portions 42, 42 (FIGS. 2A and 11) include converging inclined portions 44 and 46 that extend upwardly from the lower stepped bases 38, 38 (FIG. 1) and merge into a slot 48. As shown in FIGS. 2B and 5, an orientation sleeve 54 for the reagent package 10 depends from one of the upper stepped bases 36. Base pads 56 are provided at the lower stepped base sections 38, 38.

The glass ampoule 14 is a known closed cylindrical structure, fusion sealed at one end 57 and contains a reagent 58 (FIGS. 5 and 8) which is preferably in a dry lyophilized form to ensure that the reagent 58 remains stable for at least a two-year shelf life, for example. The glass ampoule 14 is designed to be broken under a predetermined pressure applied to each cylindrical portion 40 of the housing section 12.

Each filter screen member 16 is preferably made of a plastic material such as polypropylene and is in the form of hollow cylinder having an upper open end 60 (FIG. 1) with an upper reinforcing ring 62 of imperforate plastic. An opposite lower end 64 of the screen member 16 is of imperforate cup-shaped form. Two oppositely disposed fracture resistant imperforate vertical sections 66 and 68 extend from the upper open end 60 to the cup-shaped end 64. The imperforate vertical sections 66 and 68 are spaced by two oppositely disposed perforate vertical plastic sections 70 and 72. The filter screen member 16 can be formed in any suitable known manner such as by insert molding wherein a hollow completely perforate cylindrical form characteristic of the perforate vertical sections 70 and 72 is initially molded. The imperforate portions 64, 66 and 68 are then molded over predetermined perforate portions of the hollow cylindrical form.

The cup-shaped imperforate base section 64 of each filter screen 16 is formed with oppositely disposed V-shaped keying members 76 and 78. A detent dimple 80 is located midway between the keying members 76 and 78 on one side of the filter screen member 16.

Figure 9:
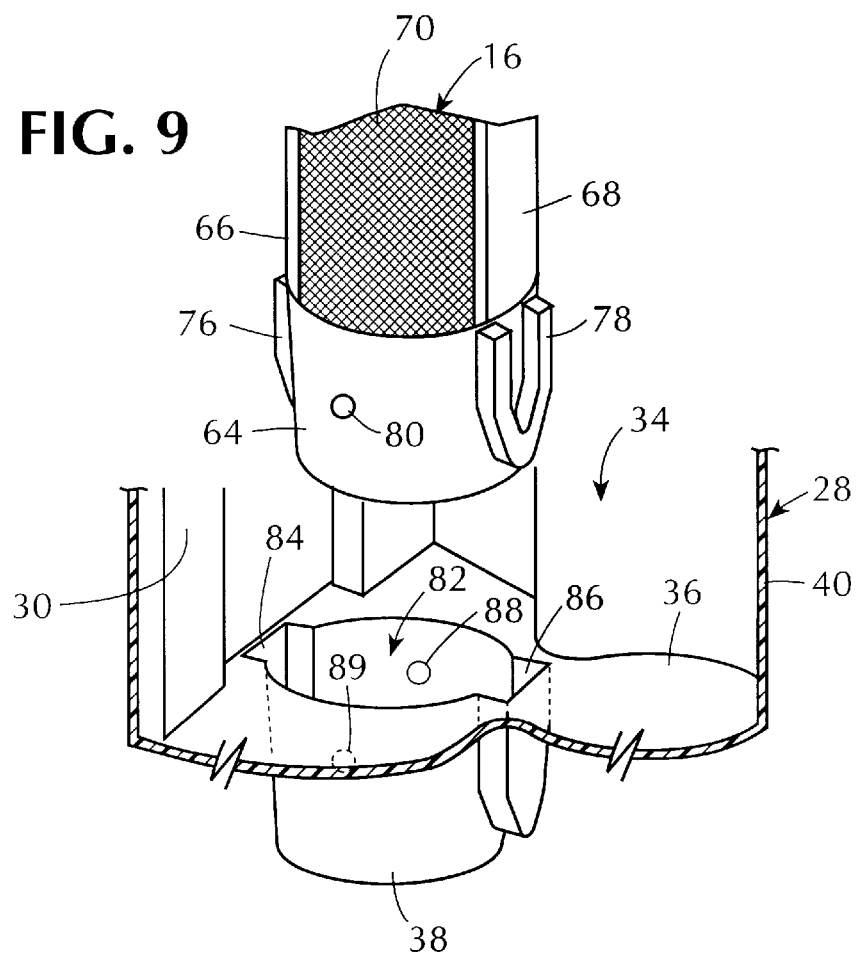
FIG. 9 is an enlarged fragmentary perspective view of a filter screen prior to insertion in a positioning well of the reagent package.
Figure 10:
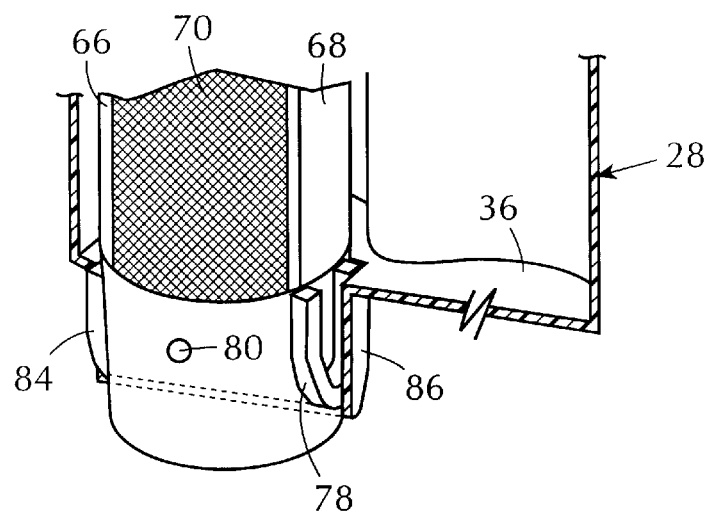
FIG. 10 is a view similar to FIG. 9 with the filter screen located in the positioning well.

Referring to FIG. 9, a positioning well 82 is formed at the lower step 38 of each of the chambers 32 and 34. The positioning well 82 includes opposite keyway slots 84 and 86 of complementary size and shape relative to the keying members 76 and 78 to locate the lower end 64 of the filter screen member 16 in a predetermined axial orientation in the respective container chambers 32 and 34. The positioning well 82 also includes opposite dimple recesses 88 and 89, one of which receives the detent dimple 80 on the filter screen 16. Engagement of the detent dimple 80 with one of the dimple recess 88, 89 detents the filter screen member 16 in the positioning well 82. Thus when the keying members 76 and 78 engage the keying slots 84 and 86 one of the fracture resistant imperforate vertical sections 66 and 68 of the filter screen member 16 can always be positioned adjacent the frangible ampoule 32 as most clearly shown in FIGS. 1, 5, and 8.

Referring to FIGS. 5, 8, 9 and 10 the cup-shaped imperforate lower end 64 of the screen member 16 occupies substantially the entire volume of the well 82. In addition the cup-shaped lower end 64 extends to the upper base portion 36 of each of the packaging sections 26 and 28. Under this arrangement little or no fluid can seep between the well 82 and the lower end 64 of the screen member 16.

With the filter screen members 16, 16 and the frangible ampoules 14, 14 located in the chambers 32 and 34, the container lid member 18 can be positioned on a top peripheral edge 90 (FIG. 1) of the container housing section 12. A peripheral gripper flange 92 is formed around the container housing section 12 slightly below the top edge 90 to facilitate sealing of the lid member 18 to the housing section 12. If desired the width of the flange 92 can be broadened or narrowed at selected locations.

The lid member 18 is a stepped structure with generally circular upper stepped end sections 94 and 96 joined to a lower stepped section 98 by risers 102 and 104. A weight reduction recess 106 is formed in each of the upper sections 94 and 96, and a position flag 108 (FIG. 1) projects beyond one end of the lid member 18 at the upper section 96. A bar code label 107 is provided on the container portion 40 below the position flag 106. A peripheral gripper flange 109 is formed around the outside border of the lid sections 94, 96 and 98, slightly above a lower peripheral edge 111 of the lid member 18. If desired the width of the flange 109 can be broadened or narrowed at selected locations. The gripper flange 109 on the lid member 18 cooperates with the gripper flange 92 on the container housing section 12 during securement of the lid member 18 to the housing section 12.

Figure 22:
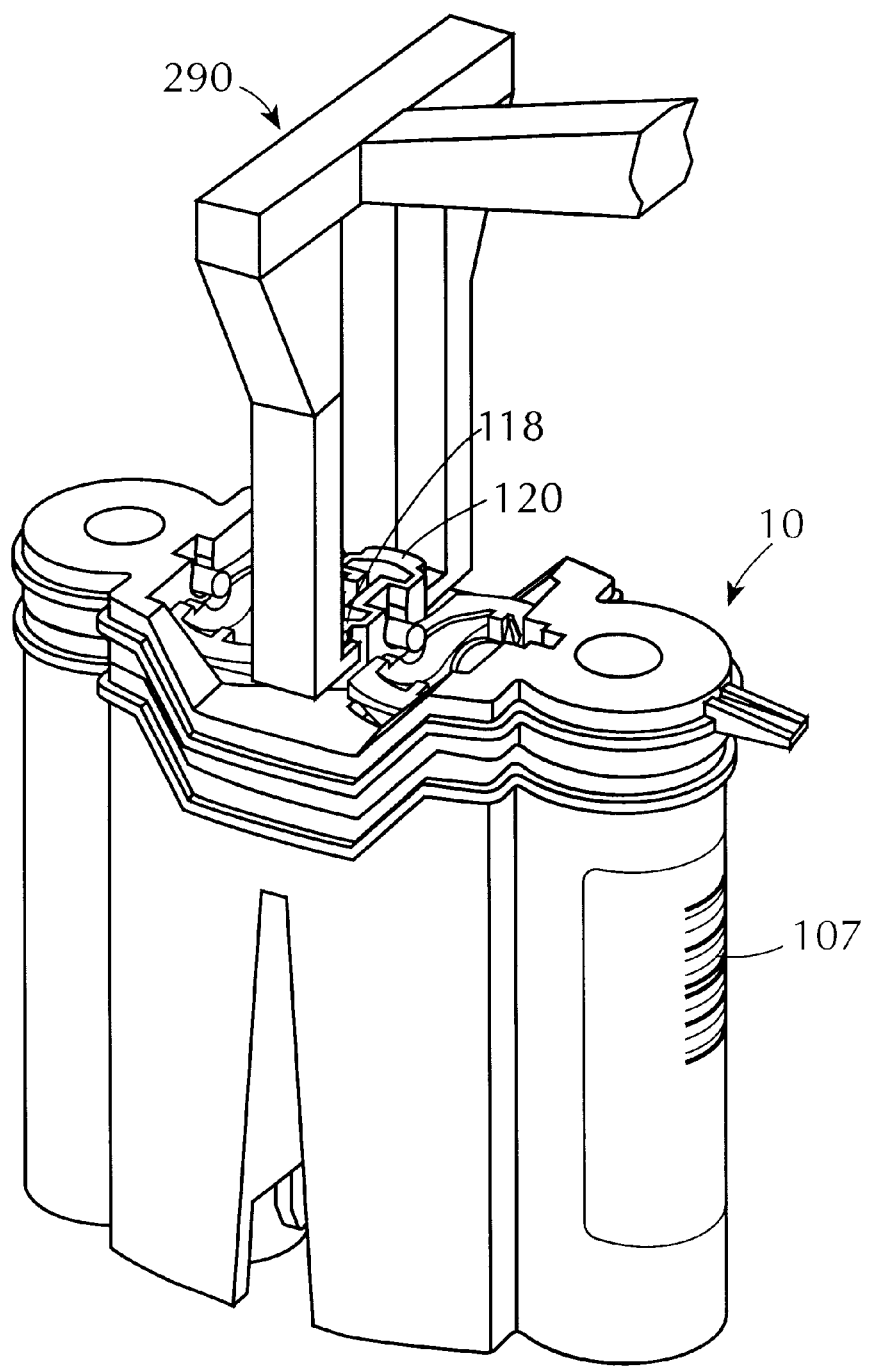
FIG. 22 is a simplified perspective view thereof with a robot device for transporting the reagent package from one location to another.

A pivot block 110 extends upwardly from the lid section 98 and includes side walls 112 and 114 spaced from the respective risers 102 and 104. The pivot block 110 also includes horizontal top flanges 118 and 120 for engagement with a robot device 121 (FIG. 22) and a weight reduction recess 116. A first pivot cradle 122 is formed in the riser 102 and a second pivot cradle 124 is formed in the side wall 112 of the pivot block 110 directly opposite the first pivot cradle 122 to accommodate the rocker valve 20. The second pivot cradle 124 includes a wide slot portion 126 (FIG. 5) and a narrow slot portion 128.

A first pivot cradle 136 similar to the first pivot cradle 122 is formed in the side wall 114 of the pivot block 110 and a second pivot cradle 138, similar to the second pivot cradle 124, is formed in the riser 104 directly opposite the first pivot cradle 136 to accommodate rocker valve 22. Corner strengthening gussets 142 are provided at opposite side ends of the risers 102, 104 and the lower section 98 of the lid member 18.

First and second lid openings 144 and 146 extend through the lower section 98 of the lid member 18 between the pivot block 110 and the risers 102 and 104. Each of the lid openings 144 and 146 is surrounded by an O-ring 148. The lid openings 144 and 146 extend through identical collars 152 and 154 (FIGS. 5 and 8) that depend from the lower lid section 98. Each of the collars 152 and 154 has a set of four depending fingers 156 that are equally spaced around the periphery of the openings 144 and 146. A necklace formation of spaced venting recesses 158 (FIG. 5) are formed in the outer peripheral surface of the collars 152 and 154 and the fingers 156.

The collars 152, 154 and the depending fingers 156 are sized to snugly engage the upper open end 60 of each filter screen 16 when the lid member 18 is positioned on the top portion of the container housing 12. The venting recesses 158 ensure that there is a vent between the collars 152, 154 and the filter screen 16 when the collars 152, 154 and their depending fingers 156 engage the open end 60 of the filter screen 16.

A stub-like projection 162 (FIG. 5) depends from an undersurface 164 of the pivot block 110 intermediate the collars 152 and 154. The projection 162 extends across the under surface 164 in alignment with the partition wall 30 of the housing section 12.

The lid member 18 supports the two rocker valves 20 and 22 for pivoted movement in side-by-side spaced relationship. Since each rocker valve 20 and 22 is identical, only the rocker valve 20 will be described in detail.

Referring to FIGS. 1, 7 and 8 the rocker valve 20 includes a curved valve face 166 having stop flanges 168 and 170 provided at respective opposite ends 174 and 176 of the valve face 166. A valve opening 172 in the valve face 166 is closer to the valve end 176 than it is to the valve end 174. A pair of valve pivots 178 and 180 project laterally from respective spaced resilient valve support arms 182 and 184. The valve support arms extend from the stop flange 170 towards the stop flange 168. The valve pivots 178 and 180 are thus cantilevered and can deflect with the valve support arms 182 and 184 toward and away from the valve face 166.

The valve pivot 178 is of uniform diameter whereas the valve pivot 180 is diametrically similar to the pivot 178 but also includes a reduced diametrical section 186 to ensure that the rocker valves 20 and 22 are positioned on the lid 18 in only one predetermined orientation.

Once the rocker valves 20 and 22 are mounted with the same orientation on the lid member 18, the valve pivot 178 of the rocker valve 20 engages the pivot cradle 122 and the valve pivot 180 engages the pivot cradle 124. The valve pivots 178 and 180 of the rocker valve 22 similarly engage the pivot cradles 136 and 138. A slightly narrowed portion 188 (FIGS. 1 and 2A) of the pivot cradles 122, 124, 136 and 138 helps detent the valve pivots 178 and 180 of each rocker valve 20,22 in their respective pivot cradles.

Under this arrangement, the rocker valves 20 and 22 are pivotally supported on the lid member 18, and the curved valve face 166 makes surface contact with the O-ring 148 that surrounds each of the lid openings 144 and 146. Thus, the curved valve face 166 and the O-ring 148 cooperate to provide a first vapor tight seal around the lid openings 144 and 146. When, the rocker valve 20 is pivoted in a first direction by pushing downwardly on the flange 170 the curved valve face 166 moves relative to the lid opening 144 from a valve open position (FIGS. 7 and 12), wherein the valve opening 172 aligns with the lid opening 144, to a valve closed position (FIG. 14) wherein an unopen portion 190 of the curved valve face 166 blocks the lid opening 144.

To assemble the reagent package 10, the filter screens 16, 16 and the glass ampoules 14, 14 are positioned in the respective chambers 32 and 34 of the container housing section 12. The lid member 18 with the rocker valves 20 and 22 pivotally supported thereon is placed on the top edge 90 of the container housing section 12. The gripper flanges 92 and 109 are gripped together in any suitable known manner to provide a pressure contact between the top edge 90 of the housing section 12 and the lower edge 111 of the lid member 18 (FIG. 5). A pressure contact is also made between a top edge 31 of the partition wall 30 and an aligned lower edge 163 of the stub-like projection 162 of the lid member 18 (FIGS. 5 and 8).

The lid member 18 and the container housing section 12 are sealed together using any suitable known sealing means such as hot plate welding. Under this arrangement, a leak-tight seal is provided between the container housing section 12 and the lid member 18. In addition, a leak-tight seal is provided between the top edge 31 of the partition wall 30 and the lower edge 163 of the stub-like projection 162 that depends from the undersurface 164 of the pivot block 110. The container chambers 32 and 34 are thus separately sealed and cannot communicate with each other.

In order to ensure that the weld between the container housing section 12 and the lid member 18 is leak tight a pressure test can be performed with pressure applied through the rocker valves in the valve open position. Pressure is transmitted in any suitable known manner to the inside chambers 32 and 34 of the reagent package and a leak check is performed around the weld portion to determine if there are any leaks.

Once the lid member 18 and the container housing section 12 are sealed together, the lid openings 144 and 146 are the only openings to the chambers 32 and 34, and outside access to the lid openings 144 and 146 is controlled by the rocker valves 20 and 22. In the valve closed position the valve face 166 is resiliently forced against the O-ring 148 by the resilient valve support arms 182 and 184 to block the lid openings 144 and 146 and provide a vapor tight seal of such openings (FIG. 14). Thus when the rocker valves 20 and 22 are in the valve closed position the container chambers 32 and 34 are closed.

The rocker valves 20 and 22 can be pivoted from the valve closed position of FIG. 14 to the valve open position of FIG. 12 by pushing downwardly on the flange 170 to pivot the valve face 166. In this manner, the valve opening 172 of each rocker valve 20, 22 aligns with the lid openings 144, 146 for example, to permit access to the container chambers 32 and 34.

When the rocker valves 20 and 22 are in the valve open position such as shown in FIG. 13 fluid can be dispensed into the container chambers 32 and 34 with a dispensation probe 192 (FIG. 13).

When a requisite amount of liquid is dispensed into the respective container chambers 32 and 34 through the aligned valve and lid openings 172, 142, and 172, 144 the rocker valves 20, 22 are pivoted to a valve closed position to provide a vapor tight seal. Pivoting of the rocker valves 20 and 22 is accomplished by pressing down upon the valve stop flanges 168, 168 until they engage the lower section 98 of the lid member 18.

The vapor tight seal between the valve faces 166, 166 and the lid openings 144 and 146 is further enhanced, especially for shipping and storage purposes, by applying the locking clip member 24 to the reagent package 10.

The locking clip 24 includes a generally rectangular bridge section 194 (FIG. 1) having opposite end portions 196 and 198 and oppositely disposed depending resilient arms 202 and 204. A generally rectangular hollow gusset 206 joins the upper middle portion of each arm 202, 204 and also joins an undersurface 205 (FIG. 5) of the bridge section 194. An elongated vertical opening 208 in each arm 202, 204 aligns with the gusset 206.

The arms 202 and 204 also include a triangular locking flange 212 that projects from an inside surface 214 of the spring arms 202 and 204 at a lower end of the vertical opening 208. A detent prong 216 is provided at an upper edge 218 of the locking flange 212 to engage a detent projection 222 (FIG. 6) that projects downwardly from an upper end of the slot 48 of the container housing section 12.

The clip arms 202 and 204 also include diverging gripper end portions 232 and 234 having knurled formations 236 at the inside surface 214 that constitute a grasping surface.

Figure 6:
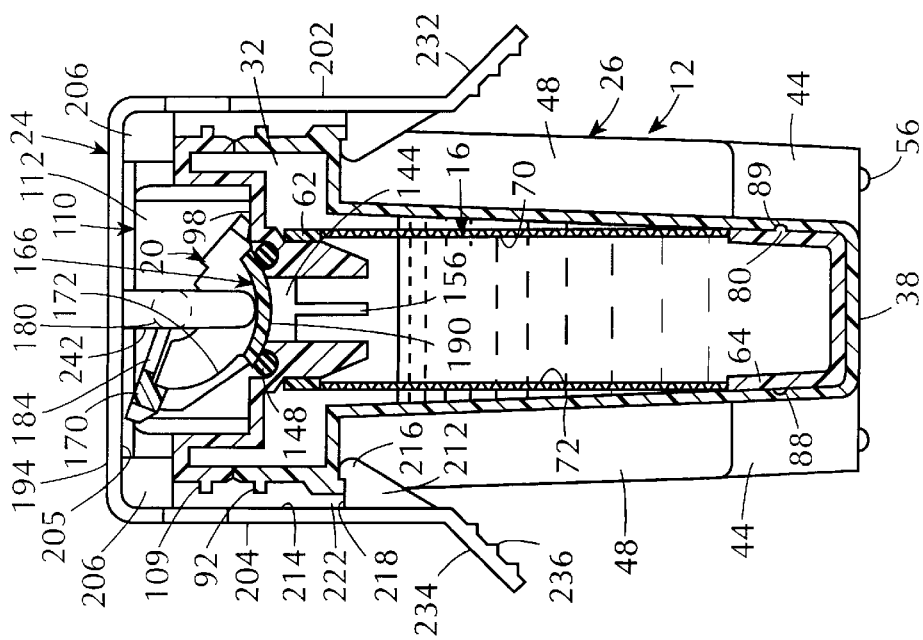
FIG. 6 is a sectional view thereof taken on the line 6—6 of FIG. 5.

The locking clip member 24 further includes a pair of spaced cylindrical pins 242 and 244 (FIGS. 1, 5 and 6) that depend from the bridge section 194 for engagement against the upper surfaces 246, 246 of the valve faces 166, 166 as shown in FIGS. 5 and 6. Although not shown a flat portion can be provided on the upper surface 246 of the curved valve face 166 to engage the free end of the cylindrical pins 242 and 244. The cylindrical pins 242 and 244 thus constitute valve face engagement members.

When the locking clip 24 is installed onto the reagent package 10 the locking flanges 212 on each of the clip arms 202 and 204 engage the detent projections 222 at opposite sides of the container housing section 28 as shown in FIG. 15. The cylindrical pins 242 and 244 thus exert a downward force on the upper surface 246 of the valve face 166 to compress the O-ring 148 and provide an enhanced pressure seal between the valve face 166 and the O-ring 148. The enhanced pressure seal between the valve face 166 and the O-ring 148 is attributable to downward deflection of the valve face 166 by the cylindrical pins 242 and 244, due to the cantilever arrangement of the valve pivots 178 and 180. The amount of deflection of the curved valve face 166 is a function of the length of the cylindrical pins 242 and 244. Preferably the pins 242 and 244 are at least a height that is sufficient to maintain the under surface 205 of the bridge section 194 elevated from the top surface end sections 94 and 96 of the container lid 18. The locking clip member 24 also serves as a shipping cover for the reagent package 10 and if desired the bridge section 194 of the locking clip 24 can be used to accommodate a label or any other package indicia.

An assembled reagent package 10 with the glass ampoules 14, 14 and the filter screen members 16, 16 can receive a reconstituting liquid in each of the chambers 32 and 34. Since the liquid installation operation for each packaging section 26 and 28 is similar, the description of this operation will focus on the packaging section 26.

Referring to FIGS. 11 and 12 the rocker valve 20 is pivoted into an open position. A predetermined amount of reconstituting liquid 193 is dispensed by the dispensation probe 192 through the open rocker valve 20 into the chamber 32. When liquid dispensation is completed the rocker valve 20 is pivoted to the valve closed position of FIG. 14 to provide a vapor tight seal of the chambers. Suitable labels (not shown) can be applied to the surface of the reagent package at the cylindrical portion 40 or the trapezoidal portion 42.

The locking clip 24 is then installed onto the reagent package 10 with the rocker valve in the valve closed position as shown in FIG. 15. The pressure enhanced valve seal provided by the locking clip 24 can enable the contents of the reagent package 10 to be adequately stored under refrigeration for up to two years without degradation.

It should be noted that when the locking clip 24 is positioned on the reagent package 10 the pressure of the cylindrical pins 242 and 244 on the curved valve surface 166 of the rocker valves 20 and 22 will restrict rotation of the curve valve face from the valve closed position to the valve open position. The bridge section 194 of the locking clip 24 also shields the rocker valves 20 and 22 from outside access and therefore prevents inadvertent movement of the rocker valves 20 and 22 from the valve closed position. Thus the reagent package 10 can be freely handled when the locking clip 24 is installed as shown in FIG. 20.

When the reagent package is ready to be used in a sample analysis system (not shown), the locking clip 24 is removed and the reagent package 10 is positioned at a known activation device of the sampling system (not shown). The activation device prepares the reagent package 10 for further processing in the sample analysis system. For example the activation device can "exercise" the locked valves 20 and 22 by opening and closing the valves a few times since they have been in a compressed state for the duration of their storage. The rocker valves 20 and 22 can then be easily pivoted due to the cantilevered arrangement of the valve pivots 178 and 180 which exert a slight downward resilient force of the face 166 against the O-rings 148.

A known bar code reader device 300 (FIGS. 1 & 21) can read the bar code label 107 on the reagent package 10 and determine from information in the bar code whether the package has ampoules or has only liquid. The type of reagents contained in the package 10 can also be determined by the bar code reader device 300. The flag portion 108 provides a physical distinguishing feature that facilitates proper orientation of the reagent package 10 in the sample handling and reagent trays (not shown) and locating a "home" position of the reagent package 10.

Figure 21:
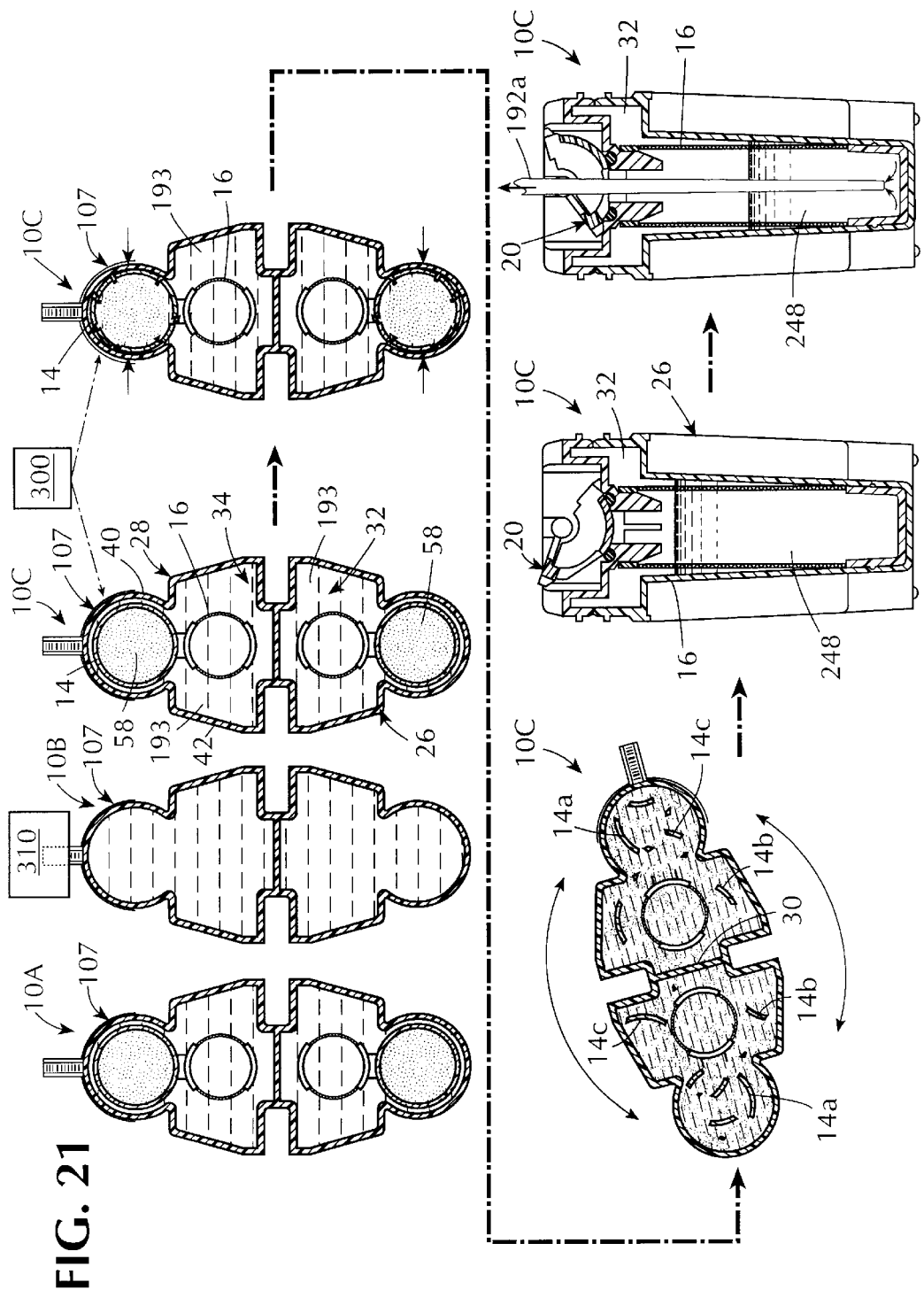
FIG. 21 is a simplified schematic representation of processing steps that include selection of a reagent package from a group, ampoule breakage in a selected reagent package, mixing of ingredients in the selected reagent package and aspiration of the mixed ingredients from the selected reagent package.

For example referring to FIG. 21, the bar code reader device 300 can select a particular reagent from an array of reagent packages such as 10A, 10B, and 10C. Based on a reading by the bar code reader device 300 of the bar code labels 107 on the reagent packages 10A, 10B and 10C the bar code reader device 300 will read one of the reagent packages such as 10C. The package 10C is brought, in a known manner to an ampoule activation-breaker device (not shown) that squeezes the cylindrical portions 40 of the packaging sections 26 and 28 until the glass ampoules 14 are broken inside the chambers 32 and 34.

When the ampoule 14 is broken by compressing the outside of the reagent package 10 at the portion 40 the breaking glass is unlikely to puncture the adjacent imperforate portion 68 of the filter screen 16. Other breaking portions of the ampoule 14 are not adjacent the filter screen 16 and therefore do not constitute a danger to the filter screen 16.

During the mixing process, the reagent package is spun and anything that is relatively heavy such as pieces of broken glass 14a, 14b, 14c and 14d tend to move away from the filter screen 16 toward the cylindrical portion 40 of the container housing section 12. Thus since the glass shards from the broken ampoule 14 will tend to move away from the imperforate portions 70 and 72 of the filter 16 there is minimal risk of damage to the filter member 16 by the spinning process. Further, the engagement of the depending fingers 156 of the lid 18 in the upper end 60 of the filter screen 16 holds the top of the filter screen 16 in engagement with the collars 152 and 154. Such engagement prevents any glass shards from entering the filter screen 16 through the upper end 60. Thus there is no opening in the filter screen member 16 for broken glass to enter.

Breakage of the ampoules 14 will enable the lyophilized ampoule ingredients 58 to mix with the reconstituting liquid 193 inside the chamber. The reagent package 10 is spun back and forth automatically by the same ampoule-activator device (not shown) to mix the ingredients inside the chamber until a desired amount of mixing is obtained resulting, in a reagent solution 248.

The reagent package 10 is preferably spun several times in one direction, stopped and then spun in a reverse direction. This spinning procedure can be repeated several times in order to obtain complete mixing of the released material from the ampoule with the reconstituting liquid inside the chamber. The spinning process causes the liquid to climb up the sides of the package and dissolve any powder that may adhere to the upper wall portions of the chambers 32 and 34 when the ampoule 14 is broken.

The mixing cycle for each reagent package can be different depending upon the type of reagent and the type of liquid in the chambers 32 and 34. Therefore the spinning cycles in opposite directions and the amount of repetition of the spinning cycles can be separately determined for packages with different reagents.

When mixing of the package ingredients is completed a robot will pick up the reagent package 10 and move it to an appropriate reagent tray (not shown). Based on information in the bar code label 107 the ampoule activator device can be directed to transport the reagent package to a predetermined reagent tray (not shown).

When the reagent package 10 is located in a selected reagent tray it is oriented such that the flag 108 faces a predetermined direction for use as an optical triggering device to help facilitate precise orientation of the reagent package 10 to an aspiration position. A predetermined amount of the reagent solution 248 is aspirated for test purposes by an aspiration probe 192a that is protracted, in any suitable known manner, into the chamber 32 for example through the rocker valve 20 when the rocker valve 20 is in the valve open position. It should be noted that the probe 192a is preferably a liquid level sensing probe such that the amount of probe projection in the chamber 32 is just enough to go below the surface of the reagent solution 248 in the chamber 32.

The probe 192a upon entering the chamber 32 through the open valve 20 projects into the hollow space or chimney of the filter screen 16. The liquid drawn into the probe 192a is thus protected by the filter screen 16 from any glass shards 14a, 14b, 14c. The filter screen 16 thus filters out and prevents any glass from the broken ampoule 14 from passing to the inside or chimney section of the filter 16. The liquid mixture in the chamber 32 thus, enters the chimney section of the filter screen 16 without glass shards 14a, 14b, 14c from the ampoule 14.

The bar code label 107 on the reagent package can also indicate the number of aspirations intended for the reagent package 10. The number of aspirations corresponds to the number of tests that the reagent package will support. A bar code reading can thus be obtained at the fill stage of the reagent package indicating the intended test capacity of the reagent package 10. Based on such reading the amount of materials 58 and 193 initially placed in the package can be predetermined to ensure that there is little or no wasted reagent solution 248.

As previously noted the lower end 64 of the screen member 16 occupies the lowest portion of the package 10 at the positioning well 82. Thus the aspiration probe 192a can reach down to the lower end 64 of the filter screen 16 to extract substantially all of the liquid reagent solution 248 that is in the reagent package 10 thereby preventing any waste of reagent solution 248.

Based on information in the bar code label 107 as to the number of tests encoded in the package 10 the sample analysis system monitor (not shown) can count the number of test doses of fluid aspirated from the reagent package 10. Thus the sample analysis system can keep an ongoing record of how many test doses have been obtained from the reagent package 10 and cease aspirations when a predetermined number of test doses are obtained.

When the contents of the reagent package are depleted, the package is transported to an exit position of the reagent tray (not shown). A robot 290 (FIG. 22) can then grasp the flanges 118 and 120 on the container lid 18 to lift the reagent package 10 and transport it to a waste receptacle (not shown).

In some instances because of test requirements the reagent package 10 need only contain a premixed liquid reagent solution. Therefore there is no need to include the glass ampoules 14 and the filter screens 16 in the reagent package 10. The reagent package 10 is thus arranged in the manner shown in FIGS. 16–20 without the glass ampoules 14, and without the filter screens 16.

A reagent liquid solution 254 is dispensed into the reagent package 10 through the valve opening 172 when the rocker valve 20 is in a valve open position (FIG. 18). When a predetermined amount of liquid has been dispensed into the reagent package 10 the rocker valve 20 is pivoted to a valve closed position as shown in FIG. 19 and the package 10 is provided with the locking clip 24 to provide an enhanced seal that prevents any outside gases from entering the chambers 32 and 34. Appropriate labels and bar coding are applied to the reagent package 10 in a manner similar to that previously described.

The reagent package 10 of FIG. 20 with liquid reagent only can be stored under refrigeration for approximately two years. When use of the reagent package 10 is desired the user removes the locking clip 24 to reduce the pressure on the rocker valves 20 and 22.

With the locking clip 24 removed from the reagent package 10 the rocker valves 20 and 22, after initial exercise movement, can be easily pivoted from the valve open position to the valve closed position and vice versa.

The reagent package 10 without the filter screen and glass ampoule also permits utilization of all liquid in the chambers 32 and 34 since the positioning well 82 in each chamber represents the lowest point of the reagent package 10. This lowest point of the reagent package 10 aligns with the valve controlled opening 142 of the reagent package 10. Thus the aspiration probe is directed toward the lowest point of the package when the aspiration process is being performed.

The two different chambers 32 and 34 of the reagent package permit containment of different reagents to carry out two different assays. However the reagent package can be provided as a single chamber structure wherein the partition wall 30 would become an outside wall. The lid member of the single chamber reagent package would have an end at the pivot block 110.

It should be noted that the robot always picks up the reagent package for transport when the rocker valves are in a valve closed position, which minimizes the possibility of interference between the robot fingers and the flanges 118 and 120 on the pivot block that are provided for engagement with the robot fingers.

Since the flag 108 and the location sleeve 54 at the base 36 are on the same end of the reagent package, the package can be oriented in a predetermined direction to ensure that the correct reagents are placed in each chamber during filling and that a record can be made in the bar code information 107 as to which chamber contains which reagents.

Robot handling of the reagent package can also be accomplished with robot finger engagement at the slot 48. The inclined surface portions 44 and 46 at the base of the container 12 facilitate positioning of the robot fingers in the slot 48.

A reagent package incorporating another embodiment of the invention is generally indicated by the reference number 290 in FIGS. 23 and 24.

The reagent package 290 includes a container housing portion 292 (FIG. 27) that accommodates two glass ampoules 294, 294, two filter members 296, 296, and a container lid 298 that supports two identical rocker valves 300 and 302 (FIG. 24). A plug member 304 (FIG. 27) is secured within the lid openings 452 and 454 of the reagent package 290 to provide a leak proof seal for the openings 452 and 454 during shipping and storage of the reagent package 290.

The reagent package 290 (FIG. 27) is a dual package with two packaging sections 306 and 308 arranged side-by-side in a manner similar to that of the packaging sections 26 and 28 of the reagent package 10. Thus the contents of either packaging section 306 and 308 cannot communicate with the contents of the other packaging section. Each of the packaging sections 306 and 308 is similar in structure and function. If desired the packaging sections 306 and 308 can be formed as separate reagent packages.

Figure 27:
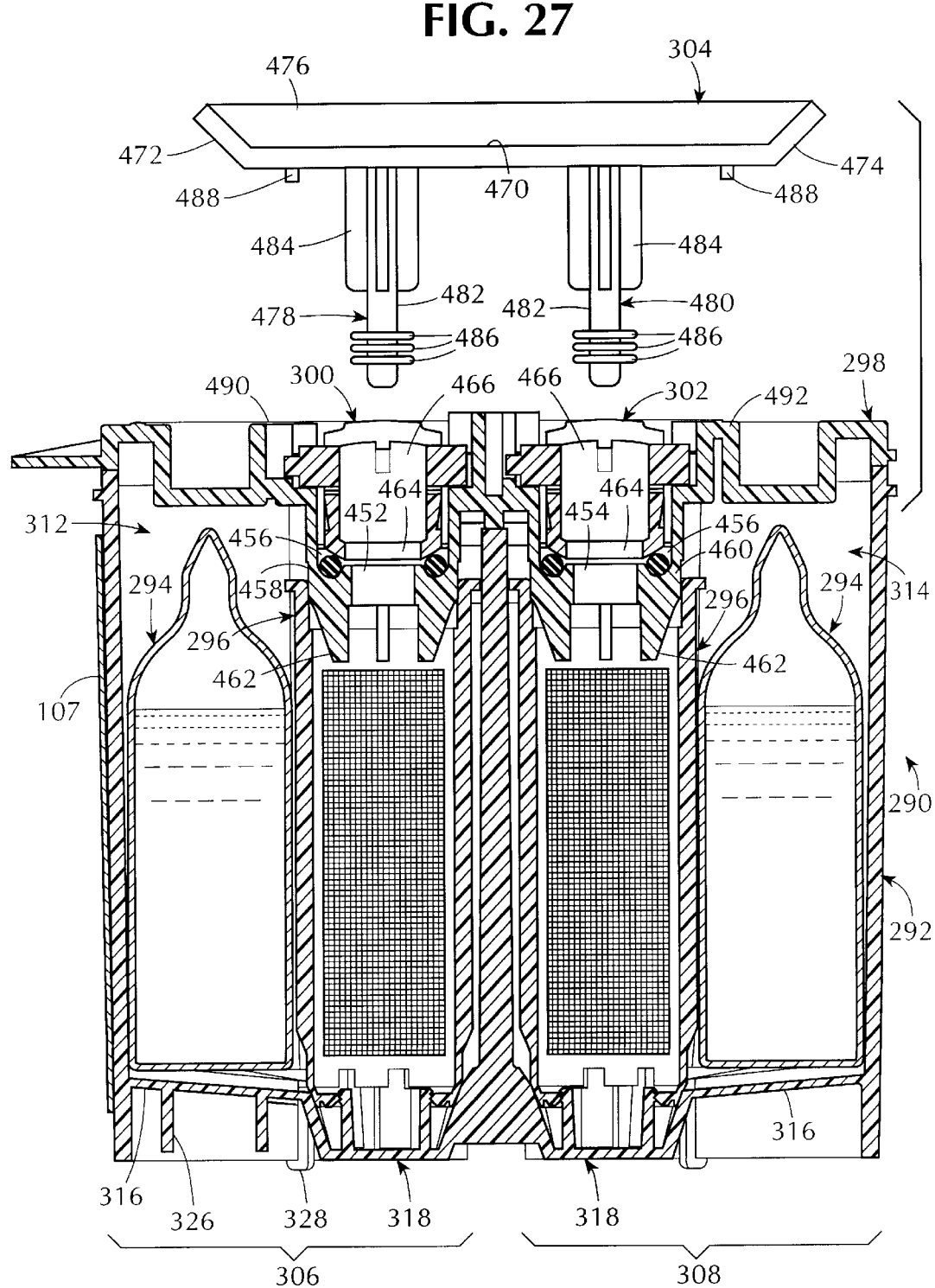
FIG. 27 is a sectional view similar to FIG. 25 with the plug member removed.
Figure 28:
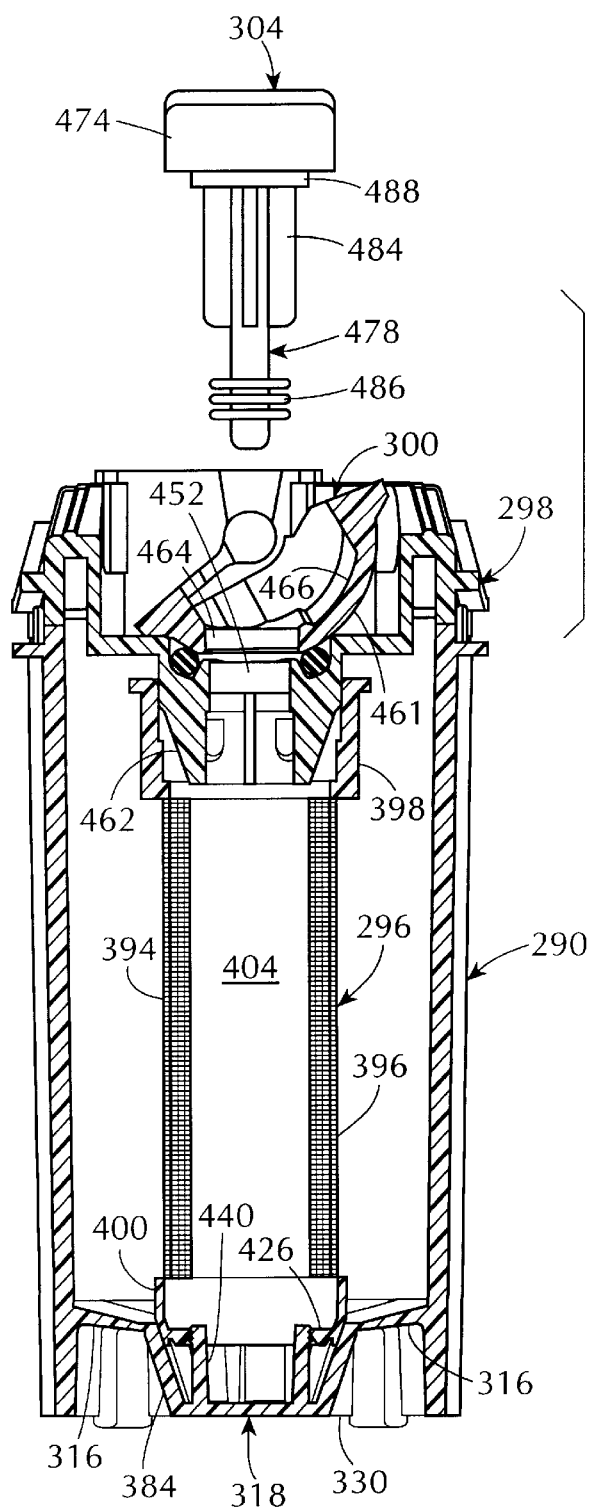
FIG. 28 is a sectional view similar to FIG. 26 with the plug member removed.
Figure 31:
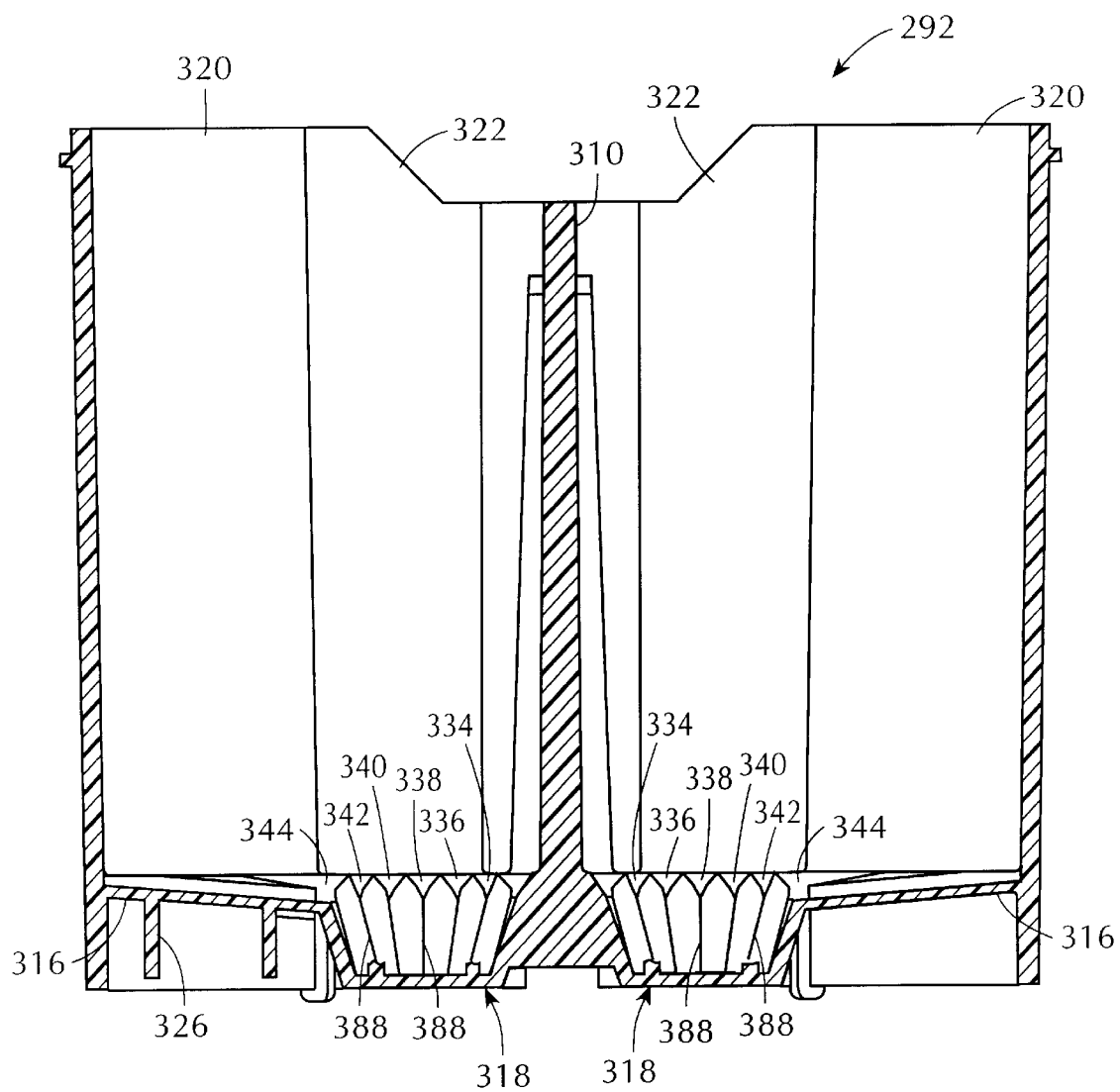
FIG. 31 is a simplified schematic elevational view thereof partly shown in section, with the latch structure in the filter wells being omitted for purposes of clarity.
Figure 32:
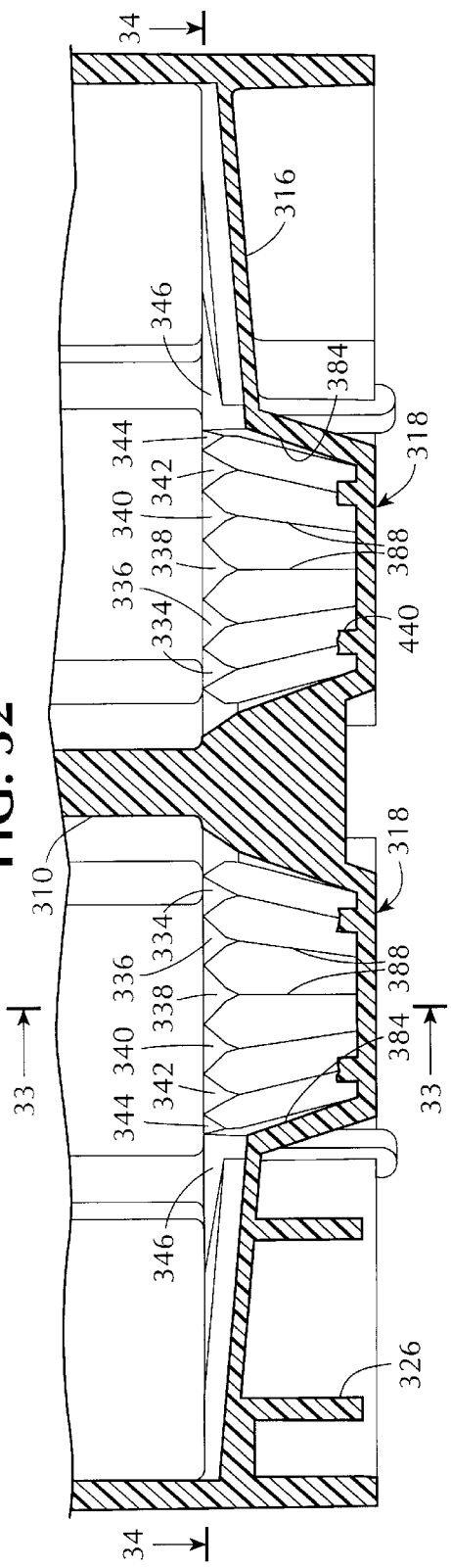
FIG. 32 is an enlarged fragmentary sectional view of a bottom portion thereof.
Figure 33:
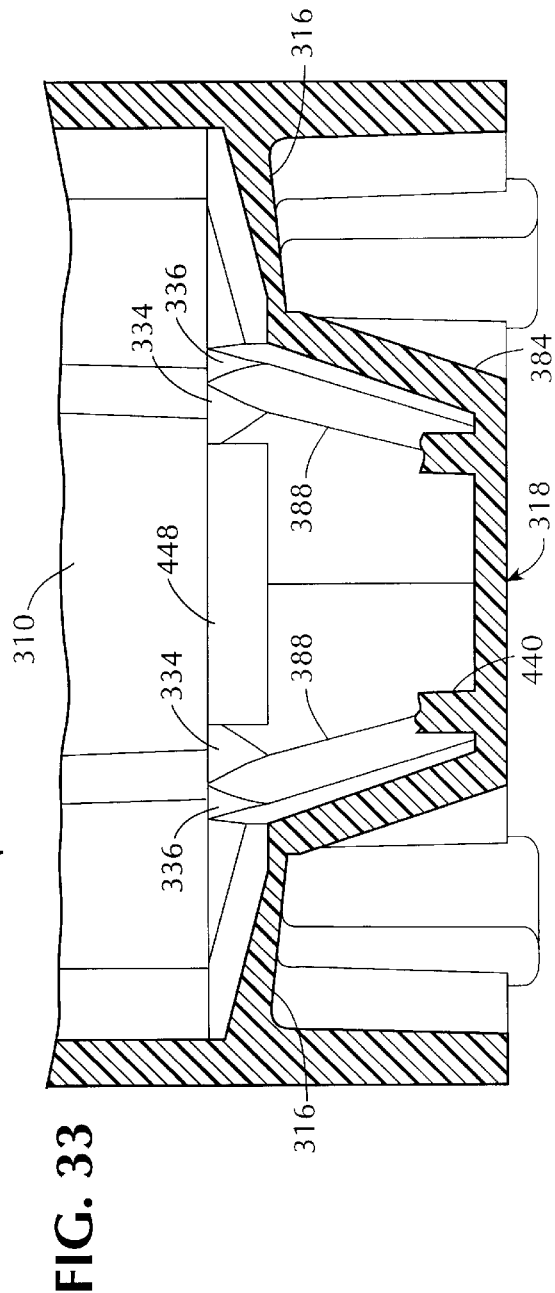
FIG. 33 is an enlarged fragmentary sectional view taken on the line 33—33 of FIG. 32.

The container housing portion 292 (FIG. 31) includes a partition wall 310 that divides the container interior into two separate container chambers 312 and 314 (FIG. 27). Each of the container chambers 312 and 314 can accommodate one of the frangible ampoules 294 and one of the filter members 296.

Figure 30:
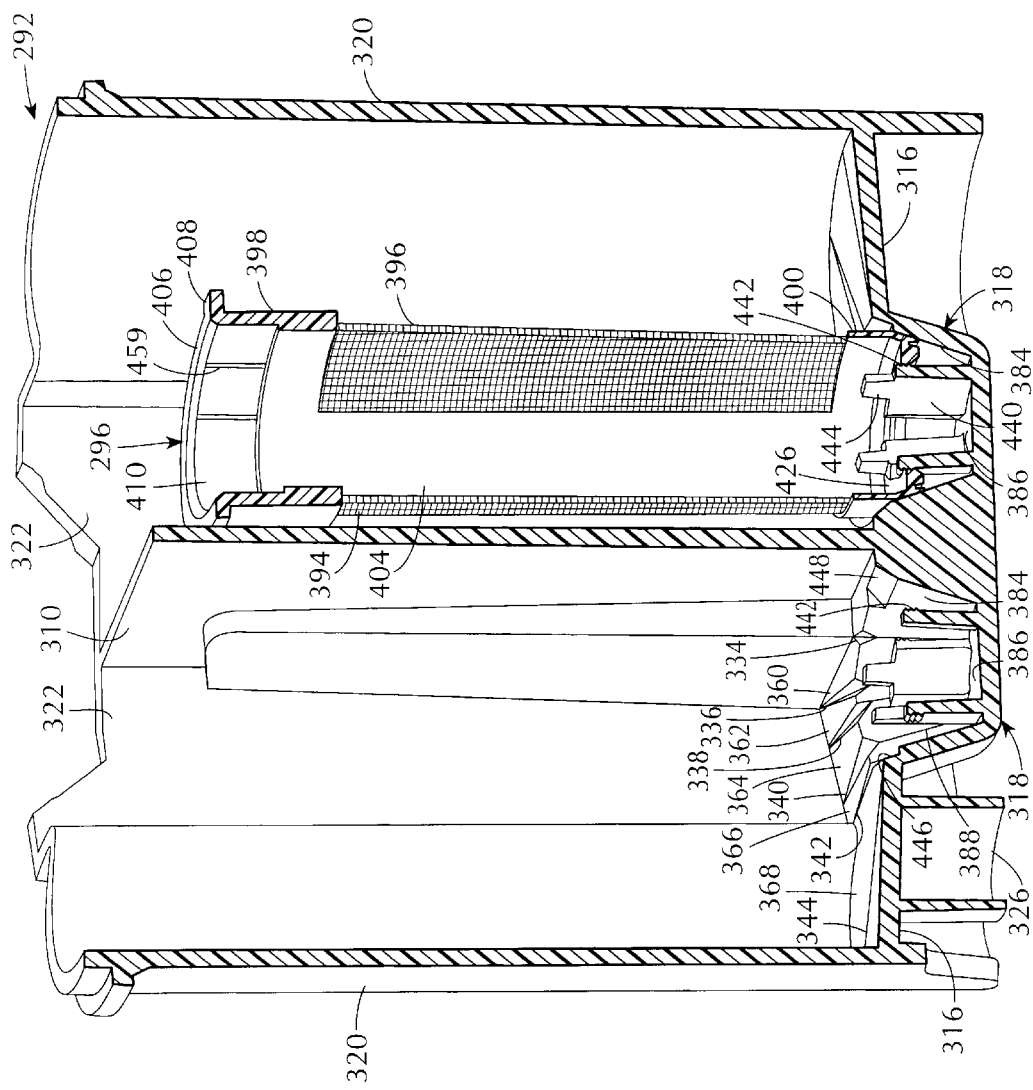
FIG. 30 is a simplified perspective view partly shown in section of the container housing portion with the filter member installed in one of the filter wells and omitted from the other filter well to more clearly show the floor channels.

Referring to FIGS. 27 and 30, each container chamber 312 and 314 has an upper stepped base portion 316 that supports the frangible ampoule 294 and a recessed well portion 318 that accommodates the filter member 296. The container housing portion 292 (FIG. 24) includes a generally cylindrical wall portion 320 that partially and closely surrounds each frangible ampoule 294 and a generally trapezoidal shaped wall section 322 that partially confines each filter member 296. Opposite vertical walls of the housing portion 292 are slightly inclined toward each other from top to bottom in a manner similar to that described with respect to the reagent package 10.

A hollow orientation sleeve 326 (FIG. 30) depends from one of the upper stepped bases 316. Footing projections or peds 328 (FIGS. 25 and 26) project below a bottom edge 330 of the container housing portion 292. The frangible ampoules 294 are structural and functional equivalents of the glass ampoules 14 of the reagent package 10 and operate in a manner similar to that previously described for the glass ampoules 14.

Figure 34:
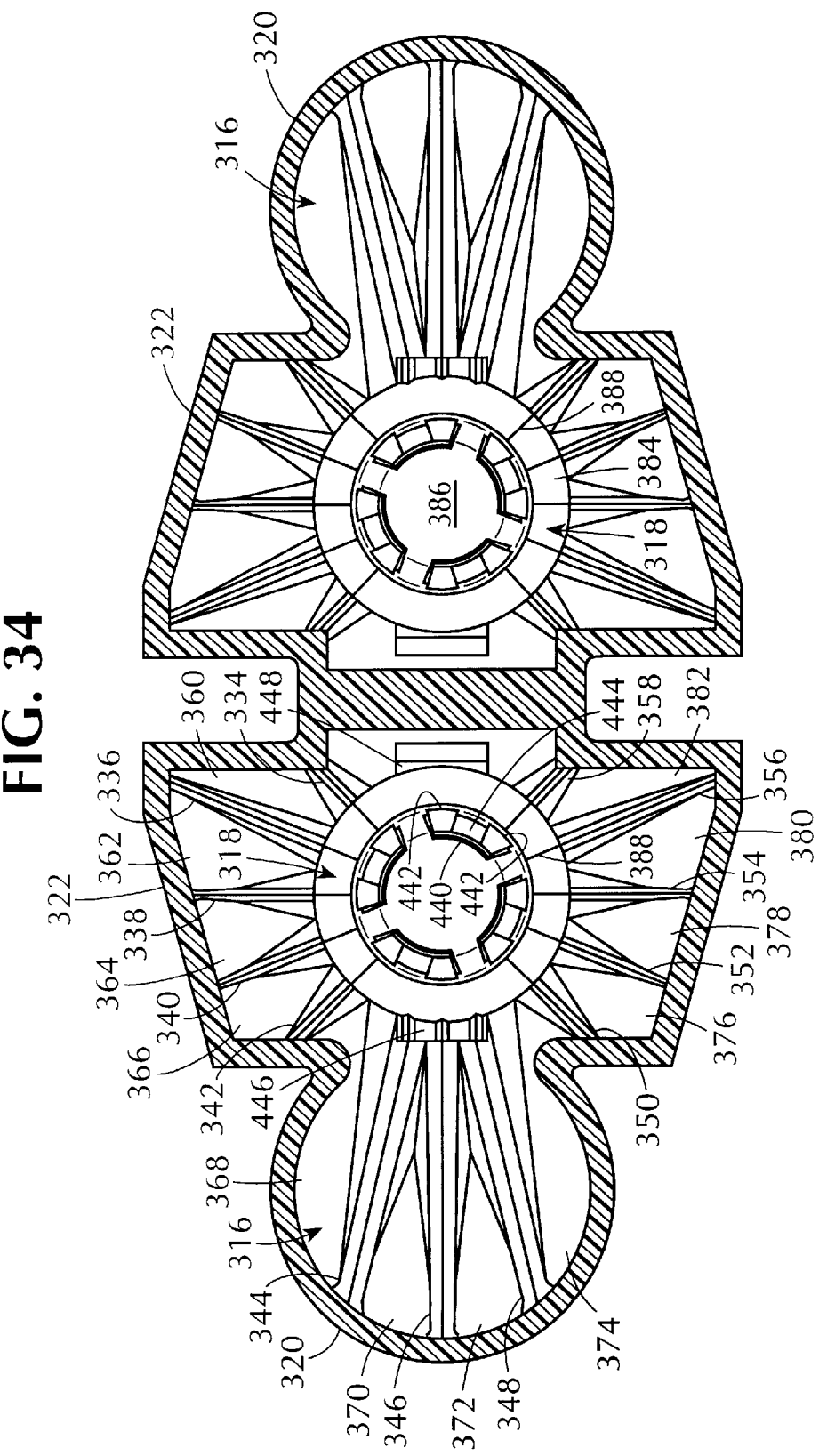
FIG. 34 is a sectional view taken on the line 34—34 of FIG. 32, and showing the floor drainage channels and the filter well latch structure that was omitted from FIGS. 31–33.

Referring to FIG. 34, the base portion 316 of the container housing section 292 is formed with a plurality of channels 334, 336, 338, 340, 342, 344, 346, 348, 350, 352, 354, 356 and 358 that are preferably V-shaped in cross section as most clearly shown in FIG. 30. The channels 334–358 are inclined downwardly toward the filter well 318 as most clearly shown by the channel 344 in FIG. 30. Also as most clearly shown in FIG. 30, the channels such as 344 are narrowest at the container wall 320 and widest at the filter well 318. Referring back to FIG. 34 a plurality of floor surface portions 360, 362, 364, 366, 368, 370, 372, 374, 376, 378, 380 and 382 that are formed between adjacent pairs of the channels 334–358 slope downwardly from an end closest to the well portion 318 toward an opposite end at the container walls 320 and 322 proximate the narrowest end of each channel.

Thus for example, the floor surfaces 362 and 364 (FIG. 30) slope downwardly toward the wall 322 such that any liquid lying on the floor surfaces 362 and 364 flows into the channels 336, 338 and 340 for movement toward the filter well 318.

Referring to FIG. 30, the well portion 318 includes an inclined well wall 384 that converges toward a base surface 386 of the well 318. The well wall 386 includes downwardly directed micro-slits or slots 388 (FIG. 30) that align with the open ends of the channels 334–358 at the filter well 318. The micro-slits 388 are formed or cut in any suitable known manner and are preferably 80 microns wide by 80 microns deep. The downwardly directed micro-slits 388 function as drainage passages for liquid to flow downwardly from the drainage channels 334–358 into the filter well 318 between the filter member 296 and the wall 384 of the filter well 318 in the manner shown in FIGS. 36 and 37.

Each filter member 296 (FIGS. 29 and 30) has the general form of a cylindrical shell which is imperforate except for oppositely disposed liquid permeable screen portions 394 and 396. The screen portions 394 extend vertically between upper and lower wall portions 398 and 400 and extend radially between oppositely disposed imperforate vertical wall portions 402 and 404. An annular rim portion 406 projects horizontally from the top of the upper wall portion 398. A stub portion 408 projects horizontally from the rim portion 406 in alignment with the screen portion 394. A pair of vent openings 412 and 414 (FIG. 29) are formed in the upper wall portion 398 in alignment with the vertical wall portion 402. A transition section 416 (FIG. 29) is provided at the lower portion of each vertical wall 402 and 404 where the vertical wall portions 402 and 404 merge into the lower wall portion 400 of the filter member 296.

The lower portion 400 (FIG. 29) of the filter member 296 includes a cylindrical section 420 and a tapered section 422 which define a lower opening 424 of the filter member 296. An inner peripheral ledge 426 which functions as a latching member is formed around the opening 424. A vertical circumferential toe flange 428 (FIGS. 29A, 29B, 35 and 36) defined by an annular recess 430 is formed at the bottom end portion of the filter member 296. The circumferential toe flange 428 contacts the wall 384 of the filter well 318 and functions as a barrier to prevent glass fragments from the ampoule 294, after it is crushed, from passing between the toe flange 428 and the wall 384 of the filter well 318.

Figure 29:
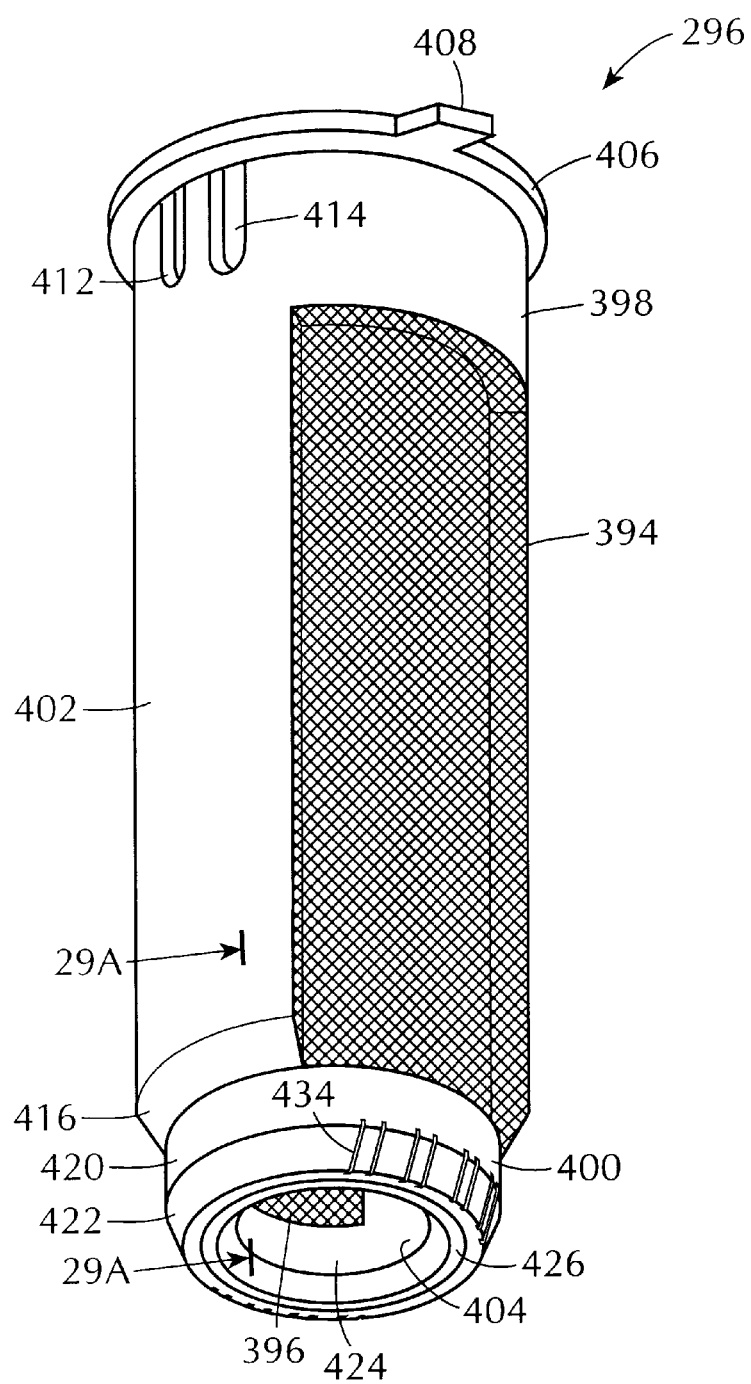
FIG. 29 is a simplified perspective view of the filter member.
Figure 29A:
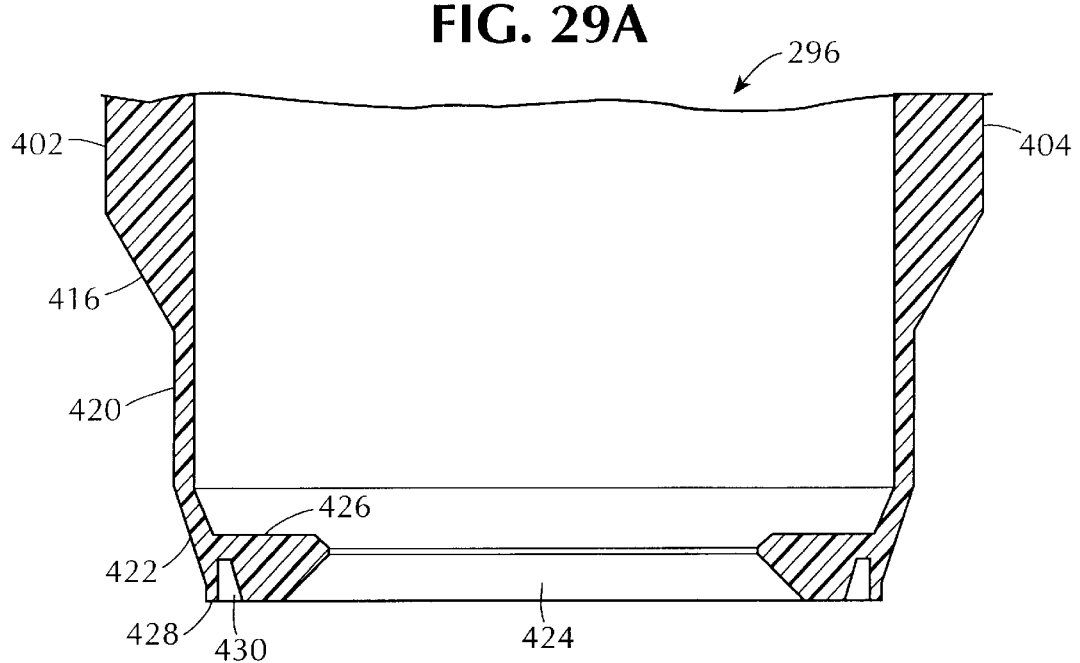
FIG. 29A is an enlarged fragmentary sectional view taken on the line 29A—29A of FIG. 29.
Figure 29B:
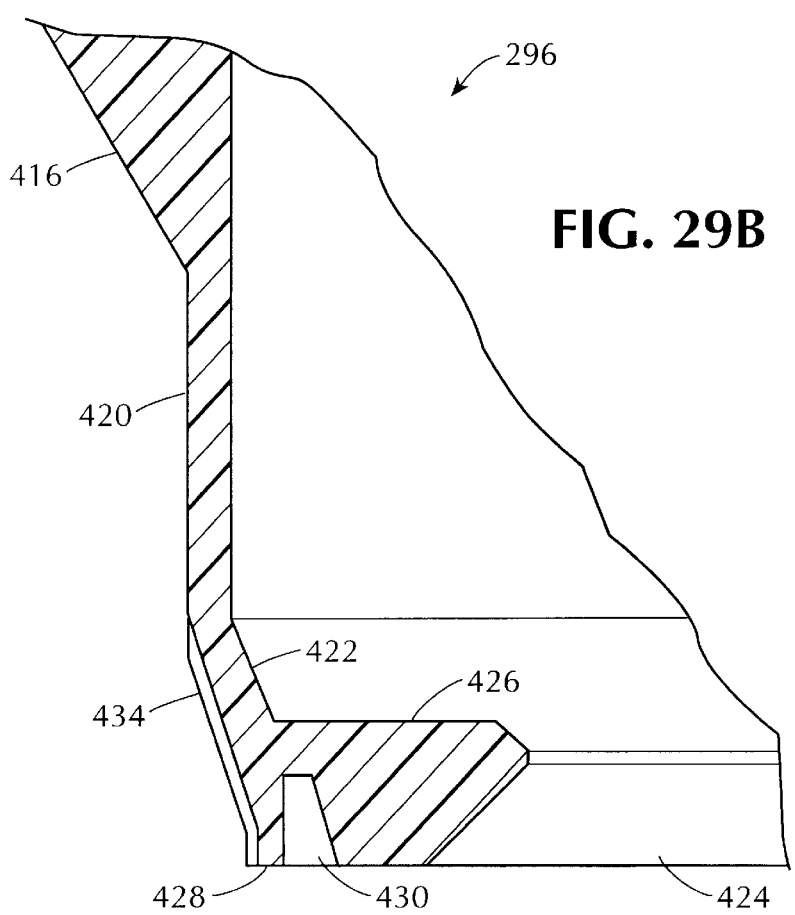
FIG. 29B is a further enlarged fragmentary detail of FIG. 29A.

As most clearly shown in FIGS. 29 and 29B spaced micro-slits or slots 434 are formed or cut into the tapered surface 422 below the screen portions 394 and 396. If desired the micro-slits 434 can be provided around the full periphery of the tapered surface 422. The micro-slits 434 are preferably approximately 80 microns wide by 80 microns deep. The micro-slits 434 function as drainage passages for liquid to flow downwardly into the filter well 318 between the tapered surface 422 of the filter member 296 and the wall 384 of the filter well 318. The filter member 296 can be molded by inserting molding in a manner similar to that previously described for the formation of the filter screen member 16. The micro slits 434 can be formed in a separate operation after the molding operation.

The wall 384 of the filter well 318 is of complementary shape and size with the tapered surface 422 of the filter member 296. The filter member 296 is receivable in the filter well 318 such that the tapered surface 422 of the filter member 296 can engage the well wall 384 to make surface contact.

Referring to FIGS. 30 and 34 four equally spaced latch members 440 extend upwardly from the base 386 of the filter well 318. The latch members 440 are diametrically spaced a predetermined amount to permit disposition of the bottom tapered surface 422 (FIG. 36) of the filter member 296 between the well wall 384 and the latch members 440. Each latch member 440 (FIGS. 30, 36 and 37) includes tooth formations 442 formed in two spaced vertical rows (FIG. 34) at opposite vertical edges of the latch member 440. The latch member 440 also includes a vertically projecting stake portion 444 (FIG. 30), which can be used to stake the filter member 296 in place in the filter well 318 in any suitable known manner.

The filter member 296 (FIGS. 30 and 35–37) is positionable in the filter well 318 such that the ledge 426 of the filter member is engagable with the tooth formation 442 of the latch members 440 to secure the filter member 296 in the well 318. The stake portion 444 can be heat staked against the annular ledge 426 of the filter member 296 to prevent removal of the filter member from the filter well 318. As described for the reagent package 10 it is preferred that one of the vertical wall portions 402 and 404 be oriented alongside an ampoule 294. The stub portion 408 is used as a alignment device. It should be noted that the orientation of the filter member in FIG. 30 is for purposes of illustrating structure and does not represent the preferred orientation as described.

When the filter member 296 is disposed in the well 318 (FIGS. 30 and 35–37) it is pushed down in the well 318 such that the peripheral ledge 426 engages the tooth formations 442 on the latch member 440. There is no particular tooth member of the tooth formations 442 that the ledge 426 should engage. Depending upon dimensional variations between the tapered surface 422 of the filter member and the well wall 384 it is anticipated that the ledge 426 can engage one of the tooth formations 442 that permit the tapered surface 422 of the filter member to contact the well wall 384.

A downwardly inclined section 446 (FIGS. 30 and 34) is provided near the filter well 318 at the end of the channels 344, 346 and 348 to enhance downward flow into the filter well. Another downwardly inclined section 448 (FIGS. 30 and 34) is provided at a downwardly directed surface 450 near the partition 310.

Figure 35:
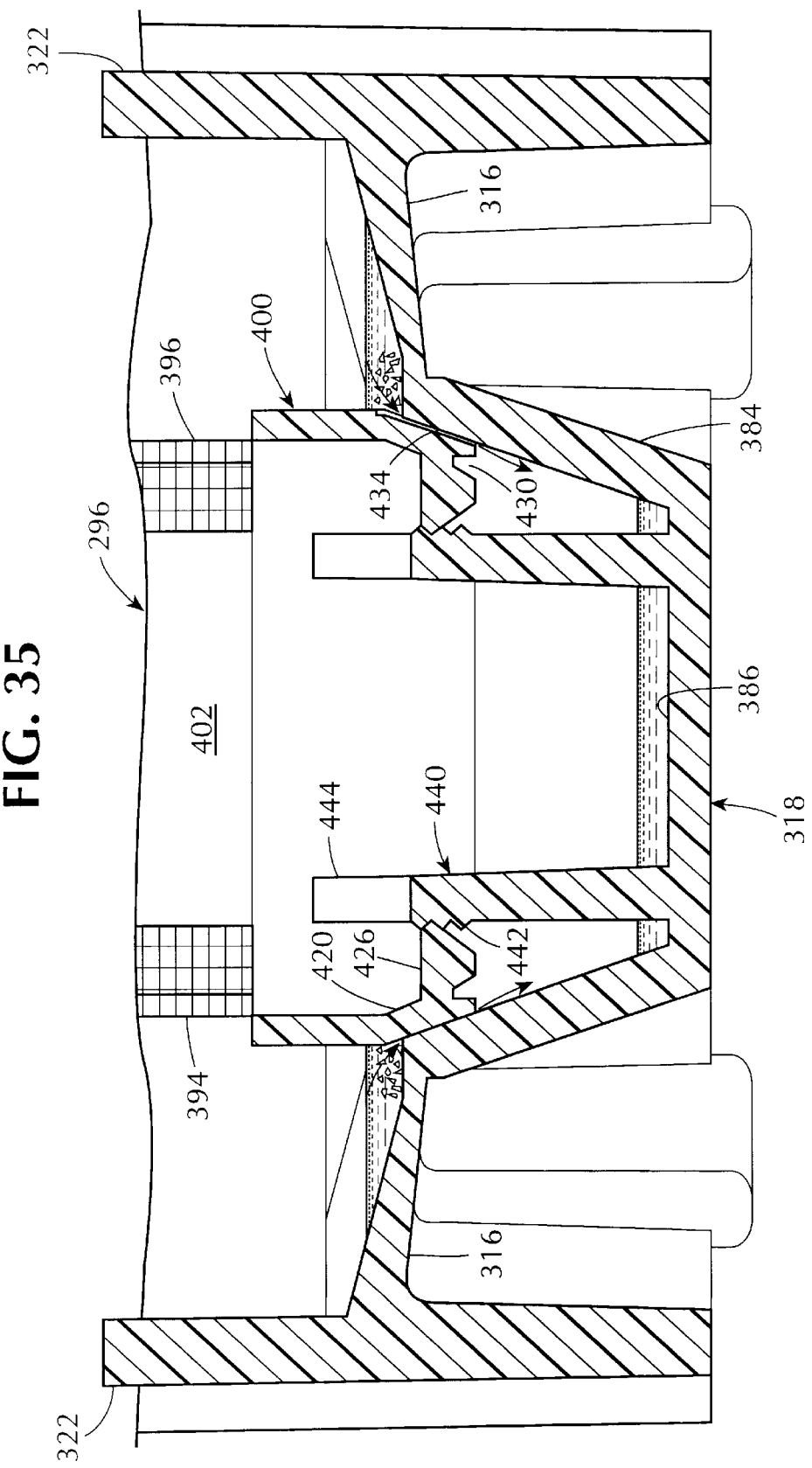
FIG. 35 is an enlarged fragmentary sectional view corresponding to FIG. 33 showing the latch structure in the filter well, engaging the filter member latch structure at the lower portion of the filter member when the filter member is installed in the filter well.
Figure 36:
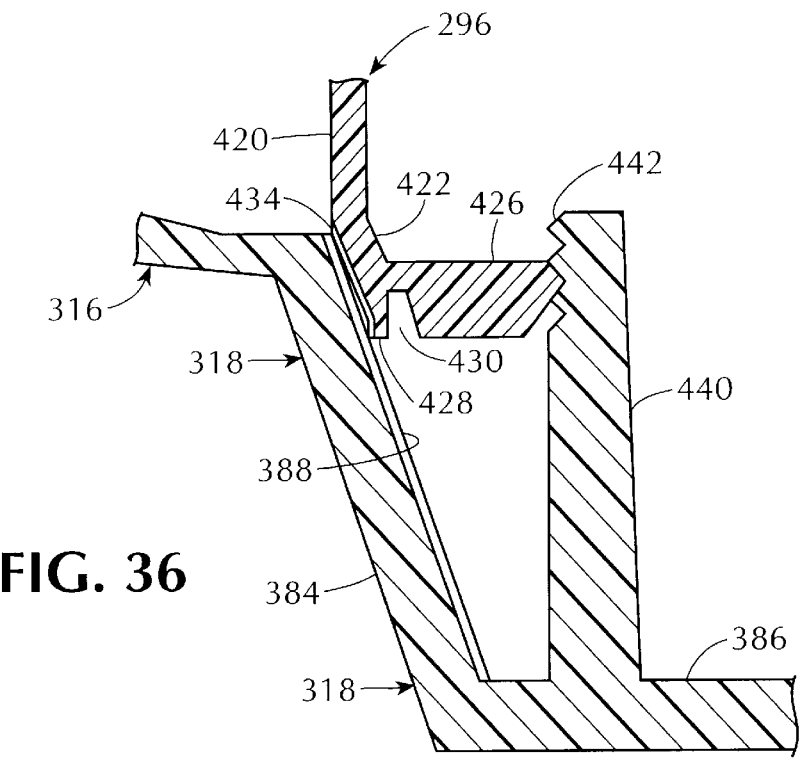
FIG. 36 is a still further enlarged fragmentary sectional view of the structure shown in FIG. 35 to show the micro-slits in the wall of the filter well.
Figure 37:
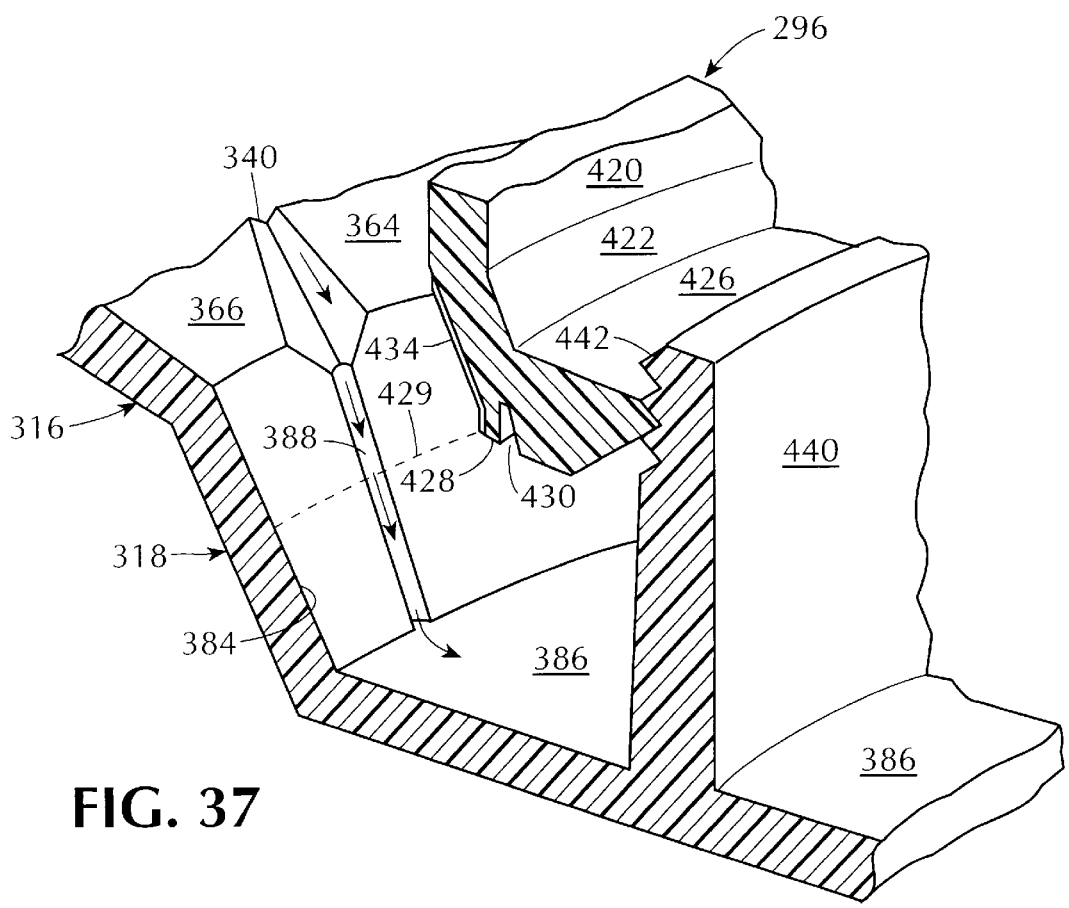
FIG. 37 is an enlarged fragmentary perspective view corresponding to FIG. 36.

The surface contact between the tapered surface 422 of the filter member 296 and the well wall 384 (FIGS. 35–37), and the circumferential line contact 429 (FIG. 37) between the circumferential toe flange 428 of the filter member 296 and the well wall 384 may permit some seepage of liquid between such surfaces. However, such surface contact is primarily intended to provide a barrier that prevents glass fragments, following the crushing of the ampoules 294, from entering the filter well 318. Aside from liquid passage through the screen portions 394 and 396 of the filter member 296 the major pathways of fluid drainage from the floor 316 of the container housing section 292 are (1) through the drainage channels 334–358 into the micro-slits 388 of the filter well 318 as shown in FIGS. 34, 36 and 37 and (2) through the micro-slits 434 formed in the tapered surface 422 and in the circumferential toe flange 428 of the filter member 296 as shown in FIGS. 35–37.

Referring to FIG. 27, the container lid 298 includes openings 452 and 454 that are surrounded by O-rings 456. The lid openings 452 and 454 are closable by the rocker valves 300 and 302 that are pivotally supported on the container lid 298 against the O-rings 456. Hollow collars 458 and 460 respectively depend from the lid 298 in alignment with the lid openings 452 and 454. Radially spaced fingers 462 extend downwardly from the hollow collars 458 and 460. The container lid 298 and the rocker valves 300 and 302 are the structural and functional equivalents of the lid 18, the collars 152 and 154, the lid openings 144 and 146 and the fingers 156 of the reagent package 10, and operate in a manner similar to that previously described for the lid member 18 and the rocker valves 20 and 22 of the reagent package 10. Thus the rocker valves 300 and 302 are movable on the container lid 298 in a manner similar to the pivotal movement of the rocker valves 20 and 22 on the container lid 18 of the reagent package 10.

The lid openings 452 and 454 (FIG. 27) represent the openings of the reagent package 290 that provide access to the chambers 312 and 314.

The collars 458 and 460 (FIG. 27) snugly engage the upper open end 410 (FIG. 30) of the filter members 296, 296. Such engagement is facilitated by vertical ribs 459 (FIG. 30) formed on the inside surface of the upper wall 398 of the filter members 296, 296 to engage the collars 458 and 460. The clearance provided by the ribs 459 and the filter vent openings 412 and 414 (FIG. 29) provide venting between the collars 458 and 460 and the filters 296, 296. The orientation stub 408 (FIGS. 29 and 30) at the annular rim 406 of the filter member 296 can be used to position the filter 296 such that the vertical wall 402 (FIG. 29) containing the vents 412 and 414 is positioned adjacent the partition wall 310 (FIG. 30) to minimize the possibility that any glass fragments can enter the hollow filter space through the vent openings 412 and 414.

The rocker valves 300 and 302 (FIG. 27) include a valve face 461 (FIG. 26) with a valve opening 464 and a closure or sealing portion 466 that is the structural and functional equivalent of the valve face 166 of the rocker valves 20 and 22.

The rocker valves 300 and 302 are thus pivotable to a valve open position as shown in FIG. 27 wherein the valve openings 464, 464 align with the openings 452 and 454 in the container lid 298. The rocker valves are also pivotable to a valve closed position similar to that of FIGS. 14 and 15 wherein the sealing portion 466 (FIG. 26) of the valve face 461 closes the container openings 452 and 454.

Assembly of the individual components of the reagent package 290 is accomplished in manner similar to that previously described for the assembly of the reagent package 10.

The plug member 304 (FIG. 27) includes an elongated support flange 470 having upwardly inclined end portions 472 and 474 and a reinforcing rib 476 projecting upwardly from the support flange 470 between the end portions 472 and 474. A pair of spaced plug portions 478 and 480 depend from the flange 470. The plug portions 478 and 480 include a shaft 482 having reinforcing gussets 484 that extend from the support flange 470 to a distance less than the full length of the shaft 482. An end portion of the shaft 482 is provided with disc shaped sealing members 486 that are vertically spaced along the shaft.

Figure 25:
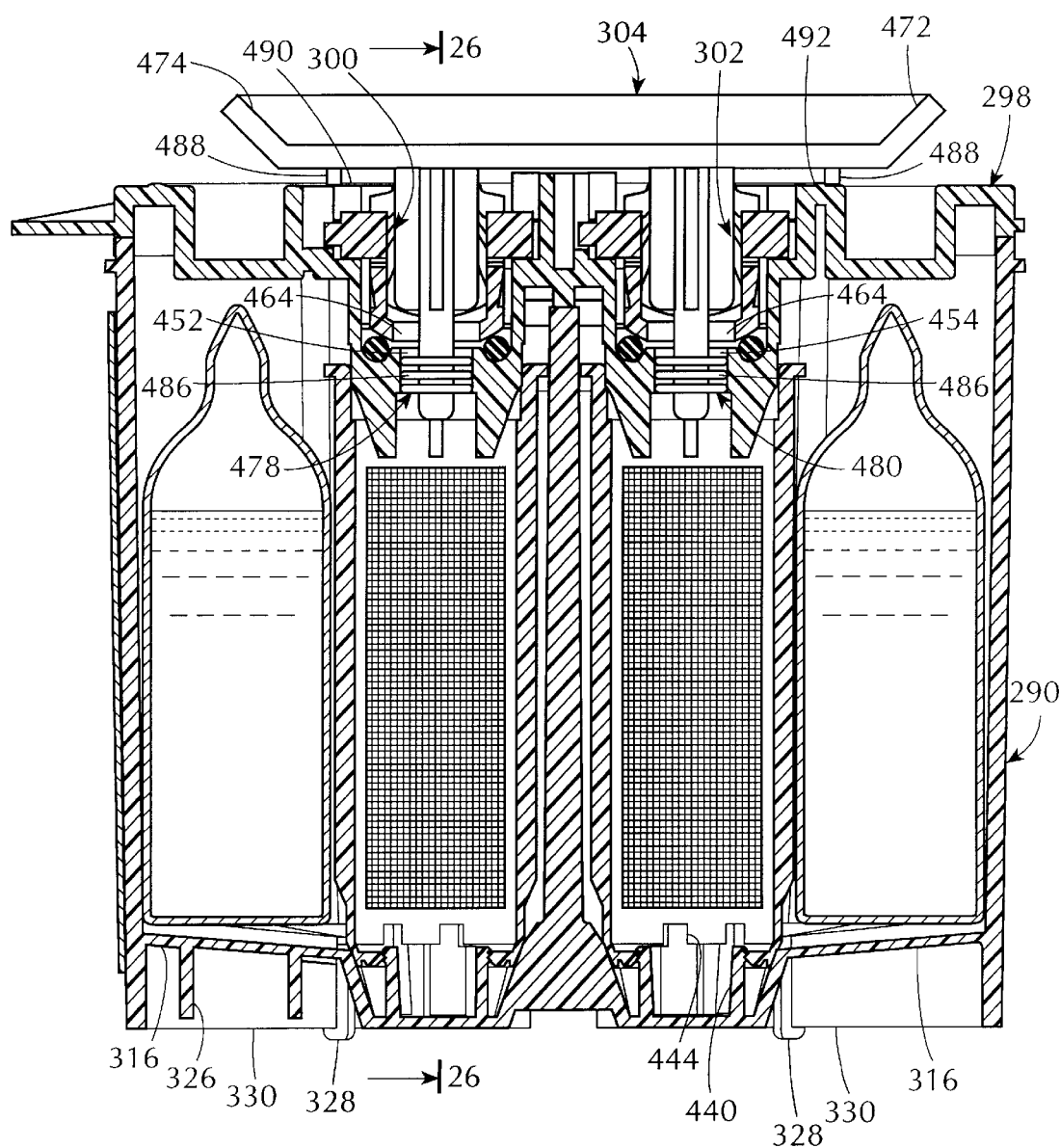
FIG. 25 is a sectional view taken on the line 25—25 of FIG. 23.
Figure 26:
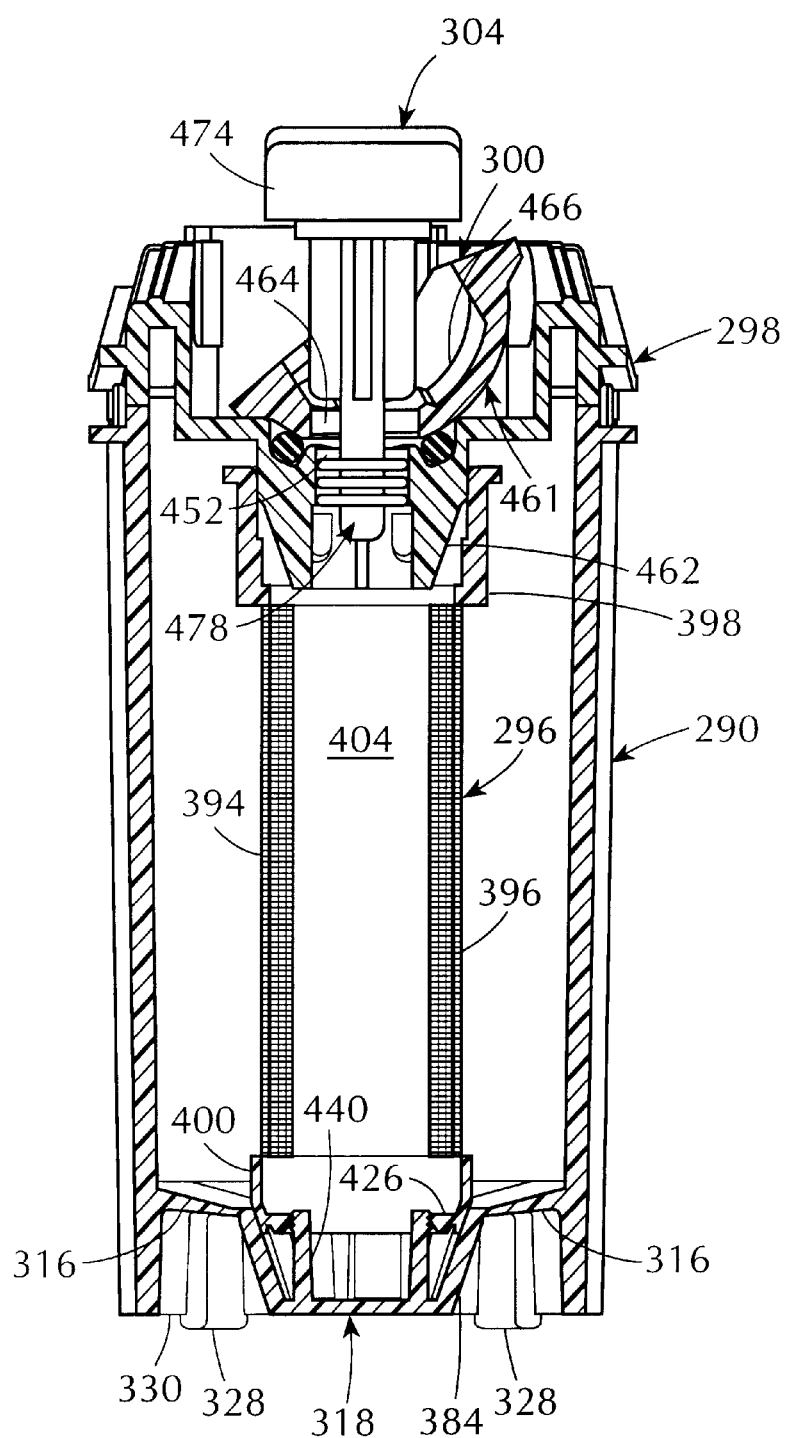
FIG. 26 is a sectional view taken on the line 26—26 of FIG. 25.

When the rocker valves 300 and 302 (FIG. 27) are in a valve open position such that the valve opening 464 aligns with the container openings 452 and 454 the plug member 304 can be secured in the openings 452 and 454 in the manner shown in FIGS. 25 and 26. Thus the plug portions 478 and 480 (FIGS. 25–27) pass through the valve openings 464, 464 and the container openings 452 and 454 to enable the sealing disks 486 of the plug member 304 to bear against the inner wall surface of the container openings 452 and 454 and thereby seal the container openings. Stop ribs 488 (FIGS. 25 and 27) are formed on the support flange 304 to abut against surfaces 490 and 492 (FIG. 25) of the lid 298 when the plug portions 478 and 480 are fully recessed in the container openings 452 and 454. With the plug member 304 in the fully recessed sealing position of FIGS. 25 and 26 the reagent package has a leak proof seal and can be transported and stored for the recommended shelf life of the reagent package.

The plug member 304 is removable from the reagent package 290 upon applying an upward force to the end portions 472 and 474 of the support flange 470. When it is desired to mix the ingredients of the reagent package 290 the plug member 304 is removed from the reagent package and the rocker valves 300 and 302 are pivoted to the valve closed position wherein the valve sealing portion 466 is positioned to close the container openings 452 and 454. The reagent package 290 is then prepared for ampoule breakage and mixing of the ampoule contents with the package ingredients outside the ampoule in a manner similar to that previously described for the reagent package 10.

Some advantages of the present invention evident from the foregoing description include a reagent package that permits self contained storage of one or more reagent components maintained separately from each other until use of a reagent mixture is desired. A further advantage is that the opening to the container is valve controlled permitting easy opening and closure of the container. The valve has the capability of providing a container seal of variable tightness such as a vapor tight seal in one instance and an enhanced pressure seal in a second instance when a pressure force is imposed on the rocker valve by the locking clip for the reagent package. Other advantages of the invention include a reagent package that can be easily opened and closed by shifting the rocker valve from a valve open position to a valve closed position. The reagent package includes structural features that permit predetermined orientation of the package to accurately identify the ingredients contained in each chamber of the package. A further advantage is that a filter screen provided in the package includes a fracture resistant section and a perforate section, the fracture resistant section being positionable adjacent a breakable ampoule to minimize the possibility of damage to the filter screen when the ampoule is broken within the container. A keying arrangement on the filter screen ensures that the filter screen is placed in a predetermined orientation within the container. A further advantage is that the container has a well portion that defines the lowest portion of the container. The well portion aligns with an aspiration probe thereby ensuring that all ingredients of the container can be drawn from the lowest portion of the container to eliminate any wasted reagent. The reagent package is structured to be easily handled manually or by a robot. A locking clip for the container locks the valves into a sufficiently leak tight condition that enables the ingredients in the container to be stored for approximately two years under refrigeration without degradation.

Further advantages of the invention are a reagent package that can be sealed independently of the valve to provide a leak proof seal and a liquid drainage system for ensuring that substantially all liquid on a floor of the reagent package can drain or seep into the aspiration area without permitting entry of any minute fragmentary glass particles that may surround the liquid aspiration area.

In view of the above, it will be seen that the several objects of the invention are achieved and other advantageous results attained.

A various changes can be made in the above constructions and method without departing from the scope of the invention, it is intended that all matter contained in the above description or shown in the accompanying drawings shall be interpreted as illustrative and not in a limiting sense.

What is claimed is:

1. A reagent package comprising,
   a) a container having a top portion with an opening and a chamber for holding liquid,
   b) a generally hollow filter member in said chamber, said filter member having an upper open end and a lower open end axially aligned with said container opening such that liquid can be drawn out of said container from the hollow portion of said filter member, through the container opening and the upper open end of the filter member,
   c) said container having a floor with a recessed filter well defining the lowest portion of said chamber, said recessed filter well having a peripheral wall,
   d) said filter member having a liquid receiving bottom portion with the lower open end and an imperforate circumferential wall surrounding said lower open end, the bottom portion of said filter member and said peripheral well wall being of a complementary shape and size such that the lower open end of said filter member is disposable in said filter well to enable the imperforate circumferential wall of said filter member to have a surface contact area with the said peripheral well wall whereby any fragmentary solid material in said chamber is prevented from entering said filter well through said surface contact area and to enable substantially all liquid received in the bottom portion of the filter member within the filter well to be drawn out of the container through the upper open end of the filter member and the container opening.

2. The reagent package as claimed in claim 1 wherein downwardly directed micro-slits are formed in the imperforate circumferential wall of said filter member where said imperforate circumferential wall is in said surface contact with said peripheral well wall to provide a drainage flow path for liquid in said chamber to flow into said filter well.

3. The reagent package as claimed in claim 1 wherein downwardly directed micro-slits are formed in said well peripheral wall where said imperforate circumferential wall of said filter member is in surface contact with said peripheral well wall to provide a drainage flow path for liquid in said chamber to flow into said well filter.

4. The reagent package as claimed in claim 1 wherein the floor of said container is formed with channels directed toward said filter well.

5. The reagent package as claimed in claim 4 wherein said channels are inclined downwardly toward said well filter.

6. The reagent package as claimed in claim 5 wherein a lowermost portion of said channels is provided at the periphery of said filter peripheral well at said well wall and wherein downwardly directed micro-slits are formed in said peripheral well wall in alignment with the lowermost portion of said channels to provide a drainage flow path for liquid in said chamber to flow into said filter well.

7. The reagent package as claimed in claim 4 wherein surface portions of said floor are defined between said channels and said surface portions are inclined to promote fluid flow on said floor into said channels.

8. The reagent package as claimed in claim 1 wherein complementary latching means are provided in said filter well and at the lower end of said filter member to detachably secure said filter in said filter well.

9. The reagent package as claimed in claim 1 wherein a circumferential toe flange is formed on one of the imperforate circumferential wall of said filter member and said well wall to make circumferential contact between said filter member and said peripheral wall to prevent any fragmentary solid matter from entering said filter well through said circumferential contact.

10. The reagent package as claimed in claim 9 wherein said circumferential toe flange is formed at the bottom of the imperforate circumferential wall of said filter.

* * * * *